(12) United States Patent
Meyer et al.

(10) Patent No.: US 8,518,539 B2
(45) Date of Patent: Aug. 27, 2013

(54) ABSORBENT STRUCTURES COMPRISING POST-CROSSLINKED WATER-ABSORBENT ARTICLES

(75) Inventors: Axel Meyer, Schwalbach (DE); Michaela Monika Czupik, Cincinnati, OH (US); Robin Lynn McKiernan, Mason, OH (US); Thomas Daniel, Waldsee (DE); Yvonne Hagen, Waldsee (DE); Ulrich Riegel, Landstuhl (DE); Dieter Hermeling, Böhl-Iggelheim (DE); Stefan Bruhns, Mannheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/277,314

(22) Filed: Oct. 20, 2011

(65) Prior Publication Data

US 2012/0101459 A1 Apr. 26, 2012

Related U.S. Application Data

(60) Provisional application No. 61/405,228, filed on Oct. 21, 2010.

(51) Int. Cl.
*B32B 5/16* (2006.01)

(52) U.S. Cl.
USPC ............... 428/403; 428/407; 427/212

(58) Field of Classification Search
USPC .................. 428/403, 407; 427/212
See application file for complete search history.

(56) References Cited

U.S. PATENT DOCUMENTS 5,032,628 A * 7/1991 Choi et al. ............... 523/409
2010/0041550 A1 2/2010 Riegel et al.

FOREIGN PATENT DOCUMENTS

| EP | 1492630 | | 1/2005 |
| WO | WO 2003/080259 A1 | | 10/2003 |
| WO | WO 2005/014064 A1 | | 2/2005 |
| WO | WO2008/092843 | * | 8/2008 |
| WO | WO 2008/092843 A1 | | 8/2008 |

OTHER PUBLICATIONS

International Search Report, PCT/US2011/056977, mailed Jan. 24, 2012, 11 pages.

* cited by examiner

*Primary Examiner* — Leszek Kiliman
(74) *Attorney, Agent, or Firm* — Andrew A Paul

(57) ABSTRACT

Absorbent structures comprising vacuum-treated (optionally coated) post-crosslinked water-absorbing polymeric particles, obtainable by vacuum-treating and optionally plasma-treating post-crosslinked water-absorbent polymeric particles (that may optionally be coated), the resulting vacuum-treated post-crosslinked water-absorbing polymeric particles having an improved absorption, whilst having good gel bed permeability.

25 Claims, No Drawings

ABSORBENT STRUCTURES COMPRISING POST-CROSSLINKED WATER-ABSORBENT ARTICLES

CROSS REFERENCE TO RELATED APPLICATION

This application claims the benefit of U.S. Provisional Application Ser. No. 61/405,228, filed Oct. 21, 2010.

FIELD OF THE INVENTION

This invention relates to improved absorbent structures comprising vacuum-treated post-crosslinked water-absorbing polymeric particles, obtainable by vacuum-treating and optionally plasma-treating post-crosslinked water-absorbent polymeric particles, the resulting vacuum-treated post-crosslinked water-absorbing polymeric particles having an improved absorption, whilst having good gel bed permeability.

BACKGROUND OF THE INVENTION

Water-absorbing polymeric particles (also referred to as superabsorbent polymer particles or superabsorbers) are widely used in absorbent articles. These are materials that are able to take up and retain several times their weight in water, possibly up to several hundred times their weight, even under moderate pressure. Absorbing capacity is usually lower for salt-containing solutions compared to distilled or otherwise de-ionised water. Typically, a superabsorbent has a centrifugal retention capacity ("CRC", as measured by the CRC method set put herein) of at least 5 g/g, preferably at least 10 g/g and more preferably at least 15 g/g. To improve their performance characteristics these water-absorbing polymeric particles are generally post-crosslinked, e.g. with organic crosslinkers. This post-crosslinking is preferably carried out as a surface post-crosslinking with ground and classified base polymeric particles.

The acrylate-based superabsorbents which dominate the market are produced by radical polymerisation of acrylic acid in the presence of a crosslinking agent (the "internal crosslinker"), usually in the presence of water, the acrylic acid being neutralized to some degree in a neutralisation step conducted prior to or after polymerisation, or optionally partly prior to and partly after polymerisation, usually by adding a alkali, most often an aqueous sodium hydroxide solution. This yields a polymer gel which is comminuted (depending on the type of reactor used, comminution may be conducted concurrently with polymerisation) and dried. Usually, the dried powder thus produced (the "base polymer") is surface crosslinked (also termed surface "post"crosslinked, or just "postcrosslinked") by adding further organic crosslinker to generate a surface layer which is crosslinked to a higher degree than the particle bulk. A polyvalent metal cation may also (alternatively or in addition) be used, such as aluminum sulphate; applying polyvalent metal cations to superabsorbent particles is regarded as "surface complexing" or as another form of surface treatment, although it has also the effect of increasing the number of bonds between individual polymer strands at the particle surface and thus increases gel particle stiffness as organic surface crosslinkers have. Organic and polyvalent metal surface crosslinkers can be cumulatively applied, jointly or in any sequence.

Surface crosslinking leads to a higher crosslinking density close to the surface of each superabsorbent particle. Although surface crosslinking decreases the CRC or other parameters describing the total absorption capacity of a superabsorbent sample, it addresses the problem of "gel blocking", and it can increase the permeability of the gel bed (measured in SFC value, as described herein); overall, the surface cross-linking may well increase the total amount of liquid that can be absorbed by a hygiene product containing a given amount of superabsorbent during normal use of the product.

There is still a need to provide even thinner absorbent articles since they increase the wearing comfort. There has been a trend to remove part or all of the absorbent cellulose fibers (pulp) from the products. Such ultrathin hygiene articles, for example diapers, may have absorbent cores that primarily comprise such water-absorbent polymeric particles, e.g. from 50% to 100% by weight of the absorbent materials in said absorbent cores. In such absorbent cores, the water-absorbing polymeric particles not only perform the storage function for the fluid but also ensure active fluid transportation (wicking absorption) and passive fluid transportation. The greater the proportion of cellulose pulp which is replaced by water-absorbing polymeric particles, the greater the number of transportation functions which the water-absorbing polymeric particles have to perform in addition to their storage function. It has been found that for such absorbent articles in particular, there is a need for water-absorbent polymeric particles that have a good absorbent capacity (CRC value) and a good fluid transportation (reflected by a good FHA value and SFC value). It is well-known in the art that there is a trade-off between the permeability and capacity/absorbency.

The need for an improved SFC has been known and examples of improved water-absorbent polymeric particles are for example described in WO 2005/014064, which for example teaches to coat a water-absorbent polymer with an elastic film-forming material.

The traditionally used absorbent cellulose fibers (pulp) serve, in addition to providing liquid absorption and transport, also to fix the water-absorbent polymeric particles. In the absence of such pulp, other fixation aids, such as fibrous thermoplastic material and/or adhesive material is used in the absorbent cores, to fix or stabilize the water-absorbent polymeric particles in the absorbent structure.

It has been noticed that this type of fixation requires a sufficiently high wicking absorption (FHA) at least in the storage layer due to the fact cellulose fibers are either not present or used in very small amounts in these novel absorbent composite structures.

The present invention therefore has for its object to provide absorbent structures, for use in hygiene articles, such as diapers and feminine hygiene articles, comprising water-absorbing polymeric particles having a good fluid transportation and preferably sufficiently high initial uptake rates, whilst having a good absorbent capacity, and in particular, such absorbents structures that comprise little or no pulp (or absorbents cellulose fibers), and that typically comprise other immobilization/structuring aids such as thermoplastic material and or adhesive materials, optionally in the form of (non-absorbing) fibers.

SUMMARY OF THE INVENTION

In one embodiment, the invention provides an absorbent structure comprising vacuum-treated, optionally coated (as described hereinafter), post-crosslinked water-absorbing polymeric particles obtainable by a process comprising the steps of:
a) obtaining, optionally coated, post-crosslinked water-absorbing polymeric particles;

b) exposing said particles of step a) to a vacuum-treatment step, at a pressure of from 0.0001 mbar to 700 mbar said particles; and c) optionally, prior to or simultaneously with step b) or subsequently to step b), treating said particles by exposing said particles to a plasma-treatment step, obtaining thus said vacuum-treated post-crosslinked water-absorbing polymer particles.

Surprisingly, the inventors found that absorbents structures comprising post-crosslinked water-absorbing polymeric particle (e.g. with high SFC) that have been surface-treated by use of a subsequent vacuum treatment step and/or by use of a subsequent vacuum and plasma treatment, have improved performance, such as reflected by its improved FHA values and/or FSR values, which is believed to be due to a surface-modification of the surface of the particles.

In some embodiments herein, said absorbent structure comprises said vacuum-treated post-crosslinked water-absorbing polymeric particles are obtainable by a process including said plasma-treatment step c).

In one embodiment, step b) and c) take place; then, steps b) may take place prior to, simultaneously with, or after step c). In one embodiment, step c) takes place simultaneously with step b).

In other embodiment herein, said step c) takes place, for example under atmospheric pressure, and either prior to or after step b), for example prior to step b).

In some embodiments herein, the plasma is air plasma.

WO 03/080259 teaches a plasma modification of absorbent using argon or nitrogen gas which results in water-absorbing materials which have a higher resistant against salt poisoning. This document however does not apply this to materials of the present invention, and it does not produce materials with high SFC (typically at least $50 \times 10^{-7}$ cm$^3$ s/g), and/or typically with improved FHA and/or improved FSR.

Said vacuum-treated post-crosslinked water-absorbing polymeric particles, or said vacuum-treated and coated (as described herein after) post-crosslinked water-absorbing polymeric particles may have, in some embodiment herein: a Centrifuge Retention Capacity (CRC; or CCRC, when applicable, as described herein after) of at least 20 g/g, or at least 25 g/g and for example up to 50 g/g; and/or an Absorbency Under Load (AUL; or CS-AUL, when applicable, as described herein after) of at least 15 g/g, preferably at least 19 g/g, or for example at least 21 g/g; and/or in some embodiments herein, a Saline Flow Conductivity (SFC; or CS-SFC, when applicable, as described herein after) of at least $50 \times 10^{-7}$ cm$^3$ s/g or at least $80 \times 10^{-7}$ cm$^3$ s/g, preferably of at least $110 \times 10^{-7}$ cm$^3$ s/g. In some embodiments herein, they may preferably have a SFC (or a CS-SFC, when applicable, as described herein after) of at least $150 \times 10^{-7}$ cm$^3$ s/g, or of at least $200 \times 10^{-7}$ cm$^3$ s/g.

Said post-crosslinked, and optionally coated, water-absorbing polymeric particles may typically have before said vacuum and optionally plasma treatment step, a SFC (or CS-SFC, as described herein, when applicable) of at least $50 \times 10^{-7}$ cm$^3$ s/g or at least $80 \times 10^{-7}$ cm$^3$ s/g, preferably of at least $110 \times 10^{-7}$ cm$^3$ s/g.

In one embodiment, said vacuum-treated post-crosslinked water-absorbing polymeric particles, vacuum-treated and coated and post-crosslinked water-absorbing polymeric particles, may have a FHA of at least 8 g/g, or for example at least 10 g/g or at least 12 g/g or at least 15 g/g.

In some embodiment, the post-crosslinked water-absorbing polymeric particles or the coated post-crosslinked water-absorbing polymeric particles, have a first FHA value and after vacuum and/or plasma treatment, said resulting vacuum-treated post-crosslinked water-absorbing polymeric particles, or said vacuum-treated and coated and post-crosslinked water-absorbing polymeric particles, have a second FHA value and said second FHA value is at least 10%, or at least 20%, or at least 30% more than said first FHA value.

In some embodiment, the post-crosslinked water-absorbing polymeric particles or the coated post-crosslinked water-absorbing polymeric particles, have a first FSR value and after vacuum and/or plasma treatment, said resulting vacuum-treated post-crosslinked water-absorbing polymeric particles, or said vacuum-treated and coated and post-crosslinked water-absorbing polymeric particles, have a second FSR value and said second FSR value is at least 10%, or at least 20%, or at least 30% more than said first FSR value.

The water-absorbing polymeric particles are surface crosslinked prior to step a), typically with an organic crosslinker.

In some embodiment the post-crosslinked water-absorbing polymeric particles are additionally coated with a film-forming polymer, or an elastic polymer or an elastic film-forming polymer, as described herein, to obtain coated post-crosslinked polymer particles; and/or in some embodiment the post-crosslinked water-absorbing polymeric particles are additionally coated with at least one water soluble polyvalent metal salt, to obtain coated post-crosslinked water-absorbing polymeric particles; and/or in some embodiments, the post-crosslinked water-absorbing polymeric particles are coated with at least one water-insoluble metal phosphate, to obtain coated post-crosslinked water-absorbing polymeric particles.

Said film forming polymer may for example have a minimum film forming temperature above –10° C. and/or said film forming polymer may comprise, or may be, a polyurethane polymer.

In some embodiments, said vacuum-treated, optionally coated, post-crosslinked water-absorbing polymer particles are such that at least 75% or at least 90% by said particles have a particle size in the range from 150 to 600 μm.

In one embodiment the absorbent substructure is an absorbent core of an absorbent article, comprising at least 50% by weight of said absorbent structure of said vacuum-treated post-crosslinked water-absorbent polymeric particles, and comprising a non-absorbent fibrous material and/or adhesive material, for example a fibrous thermoplastic material or a fibrous thermoplastic adhesive material. In one embodiment herein, the absorbent structure is an absorbent core of an absorbent article, comprising one or more core covering materials, enclosing an interior volume comprising said vacuum-treated post-crosslinked water-absorbent polymeric particles and optionally further materials, whereby said particles are present at a level of at least 65%, or at least 75% by weight of the total combined weight of said particles and optional further materials, said optional further materials for example being present and including (non-absorbing) thermoplastic polymers, e.g. in fibrous form, and/or adhesive material, e.g. in fibrous form, and/or thermoplastic adhesive material (e.g. in fibrous form). The absorbent structures or cores herein may be free of absorbent cellulose materials, and/or free absorbent fibrous materials, and whereby said absorbent core comprises a fibrous thermoplastic material and/or adhesive material.

DETAILED DESCRIPTION OF THE INVENTION

"Absorbent structure" refers to any three dimensional structure, useful to acquire and temporarily retain, or absorb and retain liquids, such as urine, menses or blood.

"Absorbent article" refers to a device that absorbs and retains liquids (such as blood, menses and urine), and more specifically, refers to devices that are placed against or in proximity to the body of the wearer to absorb and contain the various exudates discharged from the body. Absorbent articles include, but are not limited to, diapers (including diapers with fasteners, training pants, adult incontinence diapers and adult incontinence pants), adult incontinence briefs, diaper holders and liners, feminine hygiene articles, including sanitary napkins, panty-liners and the like.

"Diaper" refers to an absorbent article generally worn by infants and incontinent persons about the lower torso; infant diaper refers to baby and toddler diapers, including training pants, worn about the lower torso.

The Water-Absorbing Polymer

The water-absorbing polymer according to this invention is typically a water-absorbing polymer that has acid functions, whereby said acid functions are typically partially neutralized. The base water-absorbing polymers, when referred to herein, are dried and classified water-absorbent polymers, typically in particulate form, which may be any particulate form, including spherical particles, or sausage shaped particles, or ellipsoid shaped particles.

The water-absorbing polymers are typically produced by polymerization of a monomer solution comprising
 i) at least one ethylenically unsaturated acid functional monomer,
 ii) at least one ethylenically unsaturated crosslinker,
 iii) optionally, one or more ethylenically and/or allylically unsaturated monomers copolymerizable with i)
 iv) optionally, one or more water-soluble polymers grafted wholly or partly with the monomers i), ii) and optionally iii)
 v) optionally, in the presence of a non radical crosslinking agent, having in its single molecule two or more functional groups each of which allows formation of an ester or an amide bond by reaction with carboxyl groups.

Useful monomers i) include for example ethylenically unsaturated carboxylic acids, such as acrylic acid, methacrylic acid, maleic acid, fumaric acid, and itaconic acid, or derivatives thereof, such as acrylamide, methacrylamide, acrylic esters and methacrylic esters. Acrylic acid and methacrylic acid are particularly preferred monomers. Acrylic acid may in some embodiments be most preferable. In case acrylic acid and/or methacrylic acid is used as a component of the monomer-solution, it may be that these monomers prior to use have been stabilized with less than 250 ppm MEHQ, or for example less than 150 ppm MEHQ, more or for example less than 100 ppm MEHQ but more than 0 ppm MEHQ, and for example with 10-60 ppm MEHQ. MEHQ is the monomethylether of hydroquinone and is generally used for stabilization of acrylic acid.

The water-absorbing polymers may be crosslinked, i.e., the polymerization is carried out in the presence of compounds having two or more polymerizable groups which can be polymerized by a free-radical chain polymerization mechanism into the polymer network. Useful crosslinkers ii) include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in German patent application 103 31 450.4, mixed acrylates which, as well as acrylate groups, comprise further ethylenically unsaturated groups, as described in German patent applications 103 31 456.3 and 103 55 401.7, or crosslinker mixtures as described for example in DE-A 195 43 368, DE-A 196 46 484, WO 90/15830 and WO 02/32962.

Useful crosslinkers ii) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl esters and vinyl esters of di-, tri- or polycarboxylic acids for example tartaric acid, citric acid, adipic acid like triallylcitrate and divinyladipate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A 343 427. Useful crosslinkers ii) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention utilizes di(meth)acrylates of polyethylene glycols, the polyethylene glycol used having a molecular weight between 300 and 1000.

However, particularly advantageous crosslinkers ii) are di- and triacrylates of altogether 3- to 15-tuply ethoxylated glycerol, of altogether 3- to 15-tuply ethoxylated trimethylolpropane, especially di- and triacrylates of altogether 3-tuply ethoxylated glycerol or of altogether 3-tuply ethoxylated trimethylolpropane, of 3-tuply propoxylated glycerol, of 3-tuply propoxylated trimethylolpropane, and also of altogether 3-tuply mixedly ethoxylated or propoxylated glycerol, of altogether 3-tuply mixedly ethoxylated or propoxylated trimethylolpropane, of altogether 15-tuply ethoxylated glycerol, of altogether 15-tuply ethoxylated trimethylolpropane, of altogether 40-tuply ethoxylated glycerol and also of altogether 40-tuply ethoxylated trimethylolpropane.

In some embodiment, preferred for use as crosslinkers ii) are diacrylated, dimethacrylated, triacrylated or trimethacrylated multiply ethoxylated and/or propoxylated glycerols as described for example in prior German patent application DE 103 19 462.2. Di- and/or triacrylates of 3- to 10-tuply ethoxylated glycerol are particularly advantageous. Very particular preference may in some embodiments herein be given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual levels (typically below 10 ppm) in the water-absorbing polymer and the aqueous extracts of water-absorbing polymers produced therewith have an almost unchanged surface tension compared with water at the same temperature, typically room temperature—(typically not less than 0.068 N/m).

Examples of ethylenically unsaturated monomers iii) which are copolymerizable with the monomers i) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers iv) include polyvinyl alcohol, polyvinylpyrrolidone, starch, starch derivatives, polyglycols or polyacrylic acids, preferably polyvinyl alcohol and starch.

The preparation of a suitable water-absorbing polymer and also further useful hydrophilic ethylenically unsaturated monomers i) are described in DE-A19941423, EP-A 686 650, WO 01/45758 and WO 03/104300.

The water absorbing polymers according to the present invention may be internally crosslinked, and then the polymerization is carried with at least one ethylenically unsaturated crosslinker ii) and, optionally, in the presence of a non radical crosslinking agent v), having in its single molecule two or more functional groups each of which allows formation of an ester or an amide bond by reaction with carboxyl groups. Useful non-radical crosslinking agents v) are described below under the paragraphs of "Post-crosslinkers".

The reaction is for example carried out in a kneader as described for example in WO 01/38402, or on a belt reactor as described for example in EP-A-955 086. Alternatively it can be carried out as reverse-suspension polymerization or as a droplet-polymerization in the gas phase.

The acid groups of the hydrogels obtained are for example neutralized to a degree from 25 mol % to 90 mol %, or for example from 50 mol % to 80 mol %.

In some particular preferred embodiment the acid groups of the hydrogels obtained are preferably more than 60 mol %, more preferably more than 61 mol %, even more preferably more than 62 mol % and most preferably more than 63 mol % and preferably not more than 70 mol %, more preferably not more than 69 mol %, even more preferably not more than 68 mol % and most preferably not more than 67 mol % neutralized, for which the customary neutralizing agents can be used, for example ammonia, amines, such as ethanolamine, diethanolamine, triethanolamine or dimethylaminoethanolamine, preferably alkali metal hydroxides, alkali metal oxides, alkali metal carbonates or alkali metal bicarbonates and also mixtures thereof, in which case sodium and potassium are particularly preferred as alkali metals, but most preference is given to sodium hydroxide, sodium carbonate or sodium bicarbonate and also mixtures thereof. Typically, neutralization is achieved by admixing the neutralizing agent as an aqueous solution or else preferably as a solid material.

Neutralization can be carried out after polymerization, e.g. at the hydrogel stage. But it is also possible to neutralize up to 40 mol %, or for example from 10 to 30 mol % or for example from 15 to 25 mol % of the acid groups before polymerization by adding a portion of the neutralizing agent to the monomer solution and to set the desired final degree of neutralization only after polymerization, at the hydrogel stage. The monomer solution may be neutralized by admixing the neutralizing agent, either to a predetermined degree of preneutralization with subsequent postneutralization to the final value after or during the polymerization reaction, or the monomer solution is directly adjusted to the final value by admixing the neutralizing agent before polymerization.

Optionally any chelating agents, known to a person skilled in the art, to mask transition metals may be added to the ready-to-react monomer solution, during its preparation or into any of its components prior to mixing. Suitable chelating agents are for example—but not limited to—alkali citrates, citric acid, alkali tartrates, tartaric acid, orthophosphoric acid and its alkali salts, pentasodium triphosphate, ethylendiaminetetraacetate, nitrilotriacetic acid, and all Trilon-brands of BASF SE, Ludwigshafen like for example pentasodium-diethylene-triaminepentaacetate: Trilon® C, Trisodium-(hydroxyethyl)-ethylene-diamine-triacetate: Trilon® D, and Methylglycinediacetic acid: Trilon M®. Alkali salts in this context are salts of Li, Na, K, Rb, Cs, and ammonium.

The hydrogel can be mechanically comminuted, for example by means of a meat grinder, in which case the neutralizing agent can be sprayed, sprinkled or poured on and then carefully mixed in. To this end, the gel mass obtained can be repeatedly minced for homogenization.

A degree of neutralization which is too low may cause unwanted thermal crosslinking effects in the course of the subsequent drying and also during the subsequent post-crosslinking of the base polymer which may reduce the Centrifuge Retention Capacity (CRC) of the water-absorbing polymer substantially, When the degree of neutralization is too high, however, post-crosslinking may be less efficient, which may lead to a reduced Saline Flow Conductivity (SFC) in use.

An optimum result is obtained when the degree of neutralization of the base polymer is adjusted such as to achieve efficient post-crosslinking and thus a high Saline Flow Conductivity (SFC) while at the same time neutralization is carried on sufficiently for the hydrogel being produced to be dryable in a customary belt dryer, or other drying apparatuses customary on an industrial scale, without loss of Centrifuge Retention Capacity (CRC).

The neutralized hydrogel may (then) be dried with a belt, fluidized bed, shaft or drum dryer until the residual moisture content is below 15%, preferably below 10% by weight and in some instances, below 5% by weight, the water content being determined by the method set out below. The dried hydrogel may then be subsequently ground and sieved, useful grinding apparatus typically including roll mills, pin mills or swing mills, the sieves employed having mesh sizes necessary to produce the water-absorbing polymeric particles to give the base water-absorbing polymer.

For example less than 2% by weight, or for example less than 1.5% by weight or less than less than 1% by weight of the polymeric particles have a particle size of above 850 µm.

For example, not less than 90% by weight, or not less than 95% by weight, or for example not less than 98% by weight or for example not less than 99% by weight of the polymeric particles have a particle size in the range from 150 to 850 µm.

In one embodiment, at least 75% or at least 90% by weight of the vacuum-treated post-crosslinked water-absorbing polymeric particles have a particle size in the range from 150 µm to 700 µm or to 600 µm.

In some embodiments, preferably at least 90% by weight, or at least 95% by weight, or at least 98% by weight, or at least 99% by weight of the polymeric particles have a particle size in the range from 150 µm to 700 µm, or to 600 µm.

In other preferred embodiments, at least 90% by weight, or at least 95% by weight, or at least 98% by weight, or at least 99% by weight of the polymeric particles have a particle size in the range from 150 to 500 µm.

Usually less than 15% by weight of the polymeric particles have a particle size of less than 300 µm.

The dried base polymer used in the process of the present invention typically has a residual moisture content in the range from 0% to 13% by weight and preferably in the range from 2% to 9% by weight after drying and before application of the post-crosslinking solution.

Post-Crosslinking

The base water-absorbing polymers herein, (or optionally the coated) base polymer herein, coated with one or more of the coating agents described herein after), are subsequently surface modified by post-crosslinking, herein referred to as post-crosslinked water absorbing polymers. It should be understood that this is in addition to internal crosslinking of the base polymers, and partial surface-crosslinking on the surface of the base polymer, that may take place as described above.

Surprisingly, the inventors found that when the base polymers are post-crosslinked, as described herein after, the vacuum and optional (air) plasma treatment steps can further modify the surface of the particles, resulting in improved FSR and/or improved FHA.

Useful post-crosslinkers vi) are compounds comprising two or more groups capable of forming covalent bonds with the carboxylate groups of the polymers. Useful compounds are for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, DE-C 35 23 617 and EP-A 450 922, or B-hydroxyalkylamides as described in DE-A 102 04 938 and U.S. Pat. No. 6,239,230. It is also possible to use compounds of mixed functionality, such as glycidol, 3-ethyl-3-oxetanemethanol (trimethylolpropaneoxetane), as described in EP-A 1 199 327, aminoethanol, diethanolamine, triethanolamine or compounds which develop a further functionality after the first reaction, such as ethylene oxide, propylene oxide, isobutylene oxide, aziridine, azetidine or oxetane.

Useful post-crosslinkers vi) are further said to include by DE-A 40 20 780 cyclic carbonates, by DE-A 198 07 502 2-oxazolidone and its derivatives, such as N-(2-hydroxyethyl)-2-oxazolidone, by DE-A 198 07 992 bis- and poly-2-oxazolidones, by DE-A 198 54 573 2-oxotetrahydro-1,3-oxazine and its derivatives, by DE-A 198 54 574 N-acyl-2-oxazolidones, by DE-A 102 04 937 cyclicureas, by German patent application 103 34 584.1 bicyclic amide acetals, by EP-A 1 199 327 oxetanes and cyclic ureas and by WO 03/031482 morpholine-2,3-dione and its derivatives.

Post-crosslinking is typically carried out by spraying a solution of the post-crosslinker onto the hydrogel or the dry base-polymeric particles. Spraying is followed by thermal drying, and the post-crosslinking reaction can take place not only before but also during drying.

Preferred post-crosslinkers vi) may in some embodiments herein be amide acetals or carbamic esters of the general formula I

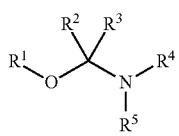

(I)

where
$R^1$ is $C_1$-$C_{12}$-alkyl, $C_2$-$C_{12}$-hydroxyalkyl, $C_2$-$C_{12}$-alkenyl or $C_6$-$C_{12}$-aryl,
$R^2$ is X or $OR^6$
$R^3$ is hydrogen, $C_1$-$C_{12}$-alkyl, $C_2$-$C_{12}$-hydroxyalkyl, $C_2$-$C_{12}$-alkenyl or $C_6$-$C_{12}$-aryl, or X,
$R^4$ is $C_1$-$C_{12}$-alkyl, $C_2$-$C_{12}$-hydroxyalkyl, $C_2$-$C_{12}$-alkenyl or $C_6$-$C_{12}$-aryl
$R^5$ is hydrogen, $C_1$-$C_{12}$-alkyl, $C_2$-$C_{12}$-hydroxyalkyl, $C_2$-$C_{12}$-alkenyl, $C_1$-$C_{12}$-acyl or $C_6$-$C_{12}$-aryl,
$R^6$ is $C_1$-$C_{12}$-alkyl, $C_2$-$C_{12}$-hydroxyalkyl, $C_2$-$C_{12}$-alkenyl or $C_6$-$C_{12}$-aryl and
X is a carbonyl oxygen common to $R^2$ and $R^3$,
wherein $R^1$ and $R^4$ and/or $R^5$ and $R^6$ can be a bridged $C_2$-$C_6$-alkanediyl and wherein the abovementioned radicals $R^1$ to $R^6$ can still have in total one to two free valences and can be attached through these free valences to at least one suitable basic structure, or polyhydric alcohols, in which case the molecular weight of the polyhydric alcohol is preferably less than 100 g/mol, or less than 90 g/mol, or less than 70 g/mol per hydroxyl group and the polyhydric alcohol has no vicinal, geminal, secondary or tertiary hydroxyl groups, and polyhydric alcohols are either diols of the general formula IIa

where $R^6$ is either an unbranched dialkyl radical of the formula —(CH2)n-, where n is an integer from 2 to 20 and or for example from 2 to 12, or for example to 4 and both the hydroxyl groups are terminal, or an unbranched, branched or cyclic dialkyl radical
or polyols of the general formula IIb

where $R^7$, $R^8$, $R^9$ and $R^{10}$ are independently hydrogen, hydroxyl, hydroxymethyl, hydroxyethyloxymethyl, 1-hydroxyprop-2-yloxymethyl, 2-hydroxypropyloxymethyl, methyl, ethyl, n-propyl, isopropyl, n-butyl, n-pentyl, n-hexyl, 1,2-dihydroxyethyl, 2-hydroxyethyl, 3-hydroxypropyl or 4-hydroxybutyl and in total 2, 3 or 4 and preferably 2 or 3 hydroxyl groups are present, and not more than one of $R^7$, $R^8$, $R^9$ and $R^{10}$ is hydroxyl,
or cyclic carbonates of the general formula III

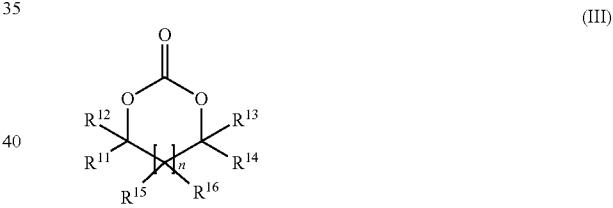

where $R^{11}$, $R^{12}$, $R^{13}$, $R^{14}$, $R^{15}$ and $R^{16}$ are independently hydrogen, methyl, ethyl, n-propyl, isopropyl, n-butyl, sec-butyl or isobutyl, and n is either 0 or 1,
or bisoxazolines of the general formula IV

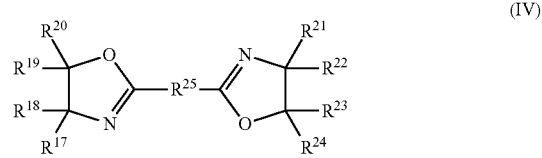

where $R^{17}$, $R^{18}$, $R^{19}$, $R^{20}$, $R^{21}$, $R^{22}$, $R^{23}$ and $R^{24}$ are independently hydrogen, methyl, ethyl, n-propyl, isopropyl, n-butyl, sec-butyl or isobutyl and $R^{25}$ is a single bond, a linear, branched or cyclic $C_1$-$C_{12}$-dialkyl radical or polyalkoxydiyl radical which is constructed of one to ten ethylene oxide and/or propylene oxide units, and is possessed by polyglycoldicarboxylic acids for example.

Preferred post-crosslinkers vi) are extremely selective. By producing and secondary reactions which lead to volatile and hence malodorous compounds are minimized. The water-absorbing polymers produced with preferred post-crosslinkers vi) are therefore odor neutral even in the moistened state.

Epoxy compounds, by contrast, may at high temperatures in the presence of suitable catalysts undergo various rearrangement reactions which lead to aldehydes or ketones for example. These can then undergo further secondary reactions which eventually lead to the formation of malodorous impurities which are undesirable in hygiene articles due to their odor. Therefore, epoxy compounds are less suitable for post-crosslinking above a temperature of about 140 to 150° C. Amino- or imino-comprising post-crosslinkers vi) will at similar temperatures undergo even more involved rearrangement reactions which tend to give rise to malodorous trace impurities and brownish product discolorations.

Polyhydric alcohols employed as post-crosslinkers vi) require high post-crosslinking temperatures due to their low reactivity. Alcohols comprising vincinal, geminal, secondary and tertiary hydroxyl groups, when employed as post-crosslinkers, give rise to byproducts which are undesirable in the hygiene sector because they lead to unpleasant odors and/or discolorations of the corresponding hygiene article during manufacture or use.

Preferred post-crosslinkers vi) of the general formula I may for example be 2-oxazolidones, such as 2-oxazolidone and N-(2-hydroxyethyl)-2-oxazolidone, N-methyl-2-oxazolidone, N-acyl-2-oxazolidones, such as N-acetyl-2-oxazolidone, 2-oxotetrahydro-1,3-oxazine, bicyclic amide acetals, such as 5-methyl-1-aza-4,6-dioxabicyclo[3.3.0]octane, 1-aza-4,6-dioxa-bicyclo[3.3.0]octane and 5-isopropyl-1-aza-4,6-dioxabicyclo[3.3.0]octane, bis-2-oxazolidones and poly-2-oxazolidones.

Preferred post-crosslinkers may in some embodiments herein be of the general formula I are 2-oxazolidone, N-methyl-2-oxazolidone, N-(2-hydroxyethyl)-2-oxazolidone and N-hydroxypropyl-2-oxazolidone.

Preferred post-crosslinkers vi) of the general formula IIa may for example be 1,3-propanediol, 1,5-pentanediol, 1,6-hexanediol and 1,7-heptanediol. Further examples of post-crosslinkers of the formula IIa are 1,3-butanediol, 1,8-octanediol, 1,9-nonanediol and 1,10-decanediol.

The diols IIa are preferably soluble in water in that the diols of the general formula IIa dissolve in water at 23° C. to an extent of not less than 30% by weight, preferably not less than 40% by weight, more preferably not less than 50% by weight and most preferably not less than 60% by weight, examples being 1,3-propanediol and 1,7-heptanediol. Even more preference is given to such post-crosslinkers are liquid at 25° C.

Preferred post-crosslinkers vi) of the general formula IIb may for example be 1,2,3-butanetriol, 1,2,4-butanetriol, glycerol, trimethylolpropane, trimethylolethane, pentaerythritol, ethoxylated glycerol, trimethylolethane or trimethylolpropane each having 1 to 3 ethylene oxide units per molecule, propoxylated glycerol, trimethylolethane or trimethylolpropane each having 1 to 3 propylene oxide units per molecule. Preference may for example be further given to 2-tuply ethoxylated or propoxylated neopentylglycol, or for example to 2-tuply and 3-tuply ethoxylated glycerol and trimethylolpropane.

Polyhydric alcohols IIa and IIb may have a 23° C. viscosity of less than 3000 mPas, preferably less than 1500 mPas, more preferably less than 1000 mPas, even more preferably less than 500 mPas and most preferably less than 300 mPas.

In some embodiments herein, particularly preferred post-crosslinkers vi) of the general formula III are ethylene carbonate and propylene carbonate.

Useful herein may be post-crosslinker vi) of the general formula IV is 2,2'-bis(2-oxazoline).

The at least one post-crosslinker vi) is used in an amount of less than 1% by weight, preferably less than 0.5% by weight, and is for example used in an amount of not more than 0.30% by weight, or for example in the range from 0.001% to 0.095% by weight, all percentages being based on the base polymer, as an aqueous solution.

It is possible to use a single post-crosslinker vi) from the above selection or any desired mixtures of various post-crosslinkers.

The aqueous post-crosslinking solution, as well as the at least one post-crosslinker vi), can typically further comprise a cosolvent.

Co-solvents which are technically highly useful are $C_1$-$C_6$-alcohols, such as methanol, ethanol, n-propanol, isopropanol, n-butanol, sec-butanol, tert-butanol or 2-methyl-1-propanol, $C_2$-$C_5$-diols, such as ethylene glycol, 1,2-propylene glycol or 1,4-butanediol, ketones, such as acetone, or carboxylic esters, such as ethyl acetate. The disadvantage with many of these cosolvents is that they have characteristic intrinsic odors. Particularly suitable cosolvents are isopropanole and 1,2-propandiole.

The co-solvent itself is ideally not a post-crosslinker under the reaction conditions. However, in a borderline case and depending on the residence time and the temperature, the cosolvent may to some extent contribute to crosslinking. This will be the case in particular when the post-crosslinker vi) is relatively unreactive and therefore is itself able to form its cosolvent, as with the use for example of cyclic carbonates of the general formula III, diols of the general formula IIa or polyols of the general formula IIb. Such post-crosslinkers vi) can also be used as cosolvent when admixed with more reactive post-crosslinkers vi), since the actual post-crosslinking reaction can then be carried out at lower temperatures and/or shorter residence times than in the absence of the more reactive crosslinker v). Since the cosolvent is used in relatively large amounts and will also remain to some extent in the product, it must be toxicologically safe.

The diols of the general formula IIa, the polyols of the general formula IIb and also the cyclic carbonates of the general formula III are also useful as cosolvents in the process of the present invention. They perform this function in the presence of a reactive post-crosslinker vi) of the general formula I and/or IV and/or of a di- or triglycidyl crosslinker. However, preferred cosolvents in the process of the present invention are in particular the diols of the general formula IIa, especially when the hydroxyl groups are sterically hindered by neighboring groups from participating in a reaction. Such diols are in principle also useful as post-crosslinkers vi), but for this require distinctly higher reaction temperatures or optionally higher use levels than sterically unhindered diols. Useful sterically hindered and hence unreactive diols also include diols having tertiary hydroxyl groups.

Examples of such sterically hindered diols of the general formula IIa which are therefore particularly useful as a co-solvent are 2,2-dimethyl-1,3-propanediol (neopentylglycol), 2-ethyl-1,3-hexanediol, 2-methyl-1,3-propanediol and 2,4-dimethylpentane-2,4-diol.

Particularly useful co-solvents in the process of the present invention further include the polyols of the general formula IIb; for example the 2- to 3-tuply alkoxylated polyols; or for example co-solvents like 3- to 15-tuply and for example 5- to 10-tuply ethoxylated polyols based on glycerol, trimethylolpropane, trimethylolethane or pentaerythritol. Seven-tuply ethoxylated trimethylolpropane is particularly useful.

Useful co-solvents further include di(trimethylolpropane) and also 5-ethyl-1,3-dioxane-5-methanol.

Particularly useful combinations of less reactive post-crosslinker vi) as cosolvent and reactive post-crosslinker vi) are combinations of polyhydric alcohols, diols of the general formula IIa and polyols of the general formula IIb, with amide acetals or carbamic esters of the general formula I.

Exemplary combinations are 2-oxazolidone/1,3-propanediol and N-(2-hydroxyethyl)-2-oxazolidone/1,3-propanediol.

Exemplary combinations further include 2-oxazolidone or N-(2-hydroxyethyl)-2-oxazolidone as a reactive crosslinker combined with 1,5-pentanediol or 1,6-hexanediol or 2-methyl-1,3-propanediol or 2,2-dimethyl-1,3-propanediol, dissolved in water and/or isopropanol as non-reactive solvent.

In some embodiments the boiling point of the at least one post-crosslinker vi) is no higher than 160° C., or no higher than 140° C. and or no higher than 120° C.; or no lower than 200° C., more preferably no lower than 220° C. and most preferably no lower than 250° C.

In some other embodiments the boiling point of cosolvent is no higher than 160° C., more preferably no higher than 140° C. and most preferably no higher than 120° C. or preferably no lower than 200° C., more preferably no lower than 220° C. and most preferably no lower than 250° C.

In yet another preferred embodiment particularly useful cosolvents in the process of the present invention therefore also include those which form a low boiling azeotrope with water or with a second cosolvent. The boiling point of this azeotrope is for example no higher than 160° C., more preferably no higher than 140° C. and most preferably no higher than 120° C. Water vapor volatile cosolvents are likewise very useful, since they can be wholly or partly removed with the water evaporating in the course of drying.

The concentration of cosolvent in the aqueous post-crosslinker solution is frequently in the range from 15% to 50% by weight, or to 40% by weight or for example in the range from 20% to 35% by weight, based on the post-crosslinker solution. In the case of cosolvents having a limited miscibility with water, it will be advantageous to adjust the aqueous post-crosslinker solution such that there is only one phase, optionally by lowering the concentration of cosolvent.

An exemplary embodiment does not utilize any cosolvent. The at least one post-crosslinker vi) is then only employed as a solution in water, with or without an added deagglomerating aid.

The concentration of the at least one post-crosslinker vi) in the aqueous post-crosslinker solution is for example in the range from 1% to 20% by weight, preferably in the range from 1.5% to 10% by weight, based on the post-crosslinker solution.

The total amount of post-crosslinker solution based on base polymer is usually in the range from 0.3% to 15% by weight or for example in the range from 2% to 6% by weight.

There are several methods to produce a post-crosslinked water-absorbing polymer having a Centrifuge Retention Capacity (CRC) of at least 25 g/g, an AUL of $\geq$15 g/g, a Saline Flow Conductivity (SFC) of at least 50 or at least 80 or at least 100 ($\times 10^{-7}$ cm$^3$ s/g) known to the person skilled in the art.

Spray nozzles useful in the process of the present invention are not subject to any restriction. Such nozzles can be pressure fed with the liquid to be spray dispensed. The atomizing of the liquid to be spray dispensed can in this case be effected by decompressing the liquid in the nozzle bore after the liquid has reached a certain minimum velocity. Also useful are one-material nozzles, for example slot nozzles or swirl or whirl chambers (full cone nozzles) (available for example from Düsen-Schlick GmbH, Germany or from Spraying Systems Deutschland GmbH, Germany). Such nozzles are also described in EP-A-0 534 228 and EP-A-1 191 051.

After spraying, the polymeric powder is thermally dried, and the post-crosslinking reaction can take place before, during or after drying.

The spraying with the solution of post-crosslinker is for example carried out in mixers having moving mixing implements, such as screw mixers, paddle mixers, disk mixers, plowshare mixers and shovel mixers. Preference may be given to vertical mixers and very particular preference to plowshare mixers and shovel mixers. Useful mixers include for example Lödige® mixers, Bepex® mixers, Nauta® mixers, Processall® mixers and Schugi® mixers.

Contact dryers are useful herein, or alternatively shovel dryers or disk dryers apparatus, in which thermal drying is carried out. Suitable dryers include for example Bepex® dryers and Nara® dryers. Fluidized bed dryers can be used as well—batch and continuous fluidized or spouted bed processes are possible.

Drying can take place in the mixer itself, for example by heating the jacket or introducing a stream of warm air. It is similarly possible to use a downstream dryer, for example a tray dryer, a rotary tube oven or a heatable screw. But it is also possible for example to utilize an azeotropic distillation as a drying process.

It may be preferred in some embodiment herein to apply the solution of post-crosslinker in a high speed mixer, for example of the Schugi-Flexomix® or Turbolizer® type, to the base polymer and the latter can then be thermally post-crosslinked in a reaction dryer, for example of the Nara-Paddle-Dryer® type or a disk dryer. The base polymer used can still have a temperature in the range from 10 to 120° C. from preceding operations, and the post-crosslinking solution can have a temperature in the range from 0 to 150° C. More particularly, the post-crosslinking solution can be heated to lower the viscosity. The post-crosslinking and drying temperature range may for example be from 30 to 220° C., especially from 150 to 210° C. or from 160 to 190° C. The residence time at this temperature in the reaction mixer or dryer is for example below 100 minutes, more preferably below 70 minutes and most preferably below 40 minutes.

The post-crosslinking dryer is flushed with air to remove vapors during the drying and post-crosslinking reaction. To augment the drying process, the dryer and the attached assemblies are ideally fully heated.

Co-solvents removed with the vapors may of course be condensed again outside the reaction dryer and optionally recycled.

After the reactive drying step has been concluded, the dried water-absorbing polymeric particles are cooled. To this end, the warm and dry polymer is preferably continuously transferred into a downstream cooler. This can be for example a disk cooler, a Nara paddle cooler or a screw cooler. Cooling is via the walls and optionally the stirring elements of the cooler, through which a suitable cooling medium such as for example warm or cold water flows. Water or aqueous solutions of additives may preferably be sprayed on in the cooler; this increases the efficiency of cooling (partial evaporation of water) and the residual moisture content in the finished product can be adjusted to a value in the range from 0% to 6% by weight, preferably in the range from 0.01% to 4% by weight and more preferably in the range from 0.1% to 3% by weight. The increased residual moisture content reduces the dust content of the product.

Optionally, however, it is possible to use the cooler for cooling only and to carry out the addition of water and additives in a downstream separate mixer. Cooling stops the reaction by lowering the temperature to below the reaction temperature and the temperature needs altogether only to be lowered to such an extent that the product is easily packable into plastic bags or into silo trucks.

Optionally, however, this moisture content can also be raised up to 75% by weight, for example by applying water in an upstream spraying mixer. The moisture content is determined by the method set out below. Such an increase in the moisture content leads to a slight preswelling of the base polymer and improves the distribution of the crosslinker on the surface and also the penetration through the particles.

The water content of the post-crosslinked, or optionally also coated (as described herein after), water-absorbing polymeric particles (prior to vacuum and/or plasma treatment) according to the present invention is for example less than 6% by weight, or less than 4% by weight and most or less than 3% by weight.

The Centrifuge Retention Capacity (CRC) of the post-crosslinked, or optionally also coated, water absorbing polymeric particles prior to vacuum and/or plasma treatment is usually at least 25 g/g, or at least 27 g/g, or at least 30 g/g and usually not above 80 g/g or not above 50 g/g.

The absorbency under a load of 4.83 kPa (AUL0.7 psi) of the post-crosslinked, or optionally also coated, water absorbing polymeric particles prior to vacuum and/or plasma treatment is for example at least 15 g/g, or at least 19 g/g, or at least 21 g/g, or at least 22 g/g and most usually not above 40 or above 30 g/g.

The Saline Flow Conductivity (SFC) of the surface-crosslinked, or optionally also coated, polymeric particles prior to vacuum and/or plasma treatment is usually at least $50 \times 10^{-7}$ cm$^3$ s/g, preferably at least $80 \times 10^{-7}$ cm$^3$ s/g, or for example at least $110 \times 10^{-7}$ cm$^3$ s/g, or for example at least $150 \times 10^{-7}$ cm$^3$ s/g or at least $180 \times 10^{-7}$ cm$^3$ s/g and usually not above $1000 \times 10^{-7}$ cm$^3$ s/g.

The Vacuum-Treatment

In one embodiment herein, the post-crosslinked, and optionally coated, water-absorbing polymeric particles herein are subjected after production (i.e. after cooling the product to below 100° C. when leaving the post-cross-linking step, (or optionally, when leaving the coating step described herein after), but typically prior to packaging, e.g. directly after said post-crosslinking step or optionally said coating step), to a vacuum treatment (with vacuum conditions).

Such vacuum-treatment is done by lowering the atmospheric pressure in a batch or continuous process step from ambient atmospheric pressure (typically around 1023 mbar but dependent on weather conditions and plant elevation level) to less than 80% ambient atmospheric pressure, or for example less than 60% ambient atmospheric pressure, or for example less than 40% ambient pressure, or for example less than 20% ambient pressure, and for example to less than 5% ambient pressure.

In one embodiment, the pressure is lowered to less than 400 mbar, preferably 20 mbar or less than 20 mbar, more preferably to 10 mbar or less than 10 mbar, most preferably to 1 mbar or less than 1 mbar, but typically not below 0.0001 mbar.

The exposure time to the vacuum conditions may be about 0.1 seconds to 30 minutes, or 0.5 seconds to 15 minutes, or 1 second to 10 minutes, or in one embodiment, more preferably 5 seconds to 5 minutes or most preferably 10 seconds to 3 minutes.

Particulate solids such as superabsorbents are frequently transported by pneumatic conveying in tubes. Typically, this involves the use of pressurized gas. It is also possible, however, to convey particles by suction. For conveying purposes, the vacuum conditions are typically set to gently move the particles to the desired place to avoid attrition problems. The vacuum applied in these conveying methods is generally not sufficient as vacuum treatment according to this invention in terms of pressure and/or exposure time. It is preferred to not combine the vacuum treatment step of this invention with a dedicated conveying step, but in particular where attrition is not a concern (that may depend on the specific superabsorbent or intended use), the vacuum treatment according to this invention may be combined with conveying by suction by adjusting the pressure and exposure time conditions accordingly. Adjusting exposure time conditions may need increasing the volume of the pneumatic conveying system by increasing the length of tubes or using extra vessels as buffer volume.

In some useful embodiments of the present invention the plasma treatment is started after the vacuum conditions are established and both treatments are executed simultaneously within the time scales for the vacuum treatment above.

In one embodiment of the present invention the plasma treatment, described below, is used in addition to the vacuum treatment; said plasma treatment may be started after the vacuum conditions are established and both treatments are then executed simultaneously within the time scales for the vacuum treatment above.

The temperature during vacuum treatment may for example be below 190° C., or for example more preferably below 140° C., even more preferably below 100° C., or for example below 60° C., or for example between 10 and 40° C.

In one embodiment, said (optionally coated) post-crosslinked water-absorbing polymeric particles have a first FSR value and after said vacuum step, or after said vacuum and said plasma treatment step(s) below, said resulting surface modified (optionally coated) post-crosslinked water-absorbing polymeric particles, have a second FSR value, and said second FSR is at least 10%, or at least 20%, or at least 30% more than said first FSR value.

(Resulting FSR values may for example be at least 0.15 g/g/s, or at least 0.16 g/g/s, or at least 0.17 g/g/s.)

The Plasma Treatment

In one embodiment, the post-crosslinked, and optionally coated, water-absorbing polymer is plasma treated. It has been found that this may not only improve the FHA as described herein, but it may simultaneously improve the FSR, in particularly when executed under vacuum conditions.

The plasma treatment step can take place prior, during or after vacuum treatment.

In some preferred embodiments, it takes place during the vacuum treatment step.

The plasma-treatment can thus take place under vacuum conditions, and in one embodiment, this is preferred; however, the plasma treatment can also take place under ambient pressure.

Both batch processes and continuous processes are known to a person skilled in the art for example to modify polymer surfaces and textiles. It is preferable to use air, including moist air and dry air; or nitrogen, argon; or water vapor; or ammonia, oxygen, carbon dioxide; organic solvent vapors, inorganic vapors or any mixture thereof as residual atmosphere for carrying out the plasma treatment; preferred are air plasma, oxygen, nitrogen, argon, water vapor, carbon dioxide and any mixture thereof, in particular air plasma.

Plasma treatment can be carried out over a wide range of pressures and temperatures. In one embodiment, a vacuum with vacuum pressures as described above is applied. In one embodiment, it is preferred to treat the water-absorbing polymeric particles at the temperature at which they leave the production process. The temperature may for example be below 190° C., more preferably below 140° C., even more preferably below 100° C., most preferably below 60° C., and particularly preferred between 10 and 40° C.

In one embodiment the precursor gas used in the generation of the plasma is, by way of example only, a noble, inert or nitrogenous gas.

Suitable types of plasma and remote plasma can be used and reference to the use of plasma can include the use of any or any combination of pulsed and/or continuous wave plasma and include non-equilibrium plasmas such as those generated by radio frequency (RF), microwaves and/or direct current. The plasma can be operated at low pressures, atmospheric or sub-atmospheric pressures to suit particular purposes.

In one embodiment, the post-crosslinked, optionally coated, water-absorbing particles are treated with water and/or water-miscible organic solvents prior to vacuum- and/or prior to plasma treatment. For example, the post-crosslinked and optionally coated water-absorbing particles are treated with 0.1 to 5% by weight (of particles) with water and/or a water miscible-organic solvent. Suitable water-miscible organic solvents are for example aliphatic $C_1$-$C_4$-alcohols, such as methanol, i-propanol and t-butanol, polyhydric alcohols, such as ethylene glycol, 1,2-propanediol and glycerol, ethers, such as methyltriglycol and polyethylene glycols having average molecular weight $M_w$ of 200-10 000 and also ketones such as acetone and 2-butanone.

In one embodiment, the (optionally coated) post-crosslinked water-absorbing polymeric particles have a first FHA value, and after said vacuum and/or plasma treatment, or in particular after said vacuum treatment step and said (additional or simultaneous) plasma treatment step, said resulting surface-modified (optionally coated) post-crosslinked water-absorbing polymeric particles have a second FHA, and said second FHA is at least 10%, or at least 20%, or at least 30% more than said first FHA.

In one embodiment, the vacuum-treated post-crosslinked (or optionally also coated, as described herein) water-absorbing polymeric particles, submitted to said vacuum treatment step and to optionally, or for example, said plasma treatment step, may have a FHA of at least 8 g/g, or for example at least 10 g/g or at least 12 g/g or at least 15 g/g, or at least 20 g/g, or at least 23 g/g.

In some embodiment herein, the post-crosslinked water-absorbing polymeric particles are produced by
a) polymerization of a monomer solution comprising
   i) at least one ethylenically unsaturated acid functional monomer,
   ii) at least one ethylenically unsaturated crosslinker,
   iii) optionally one or more ethylenically and/or allylically unsaturated monomers copolymerizable with i),
   iv) optionally, one or more water-soluble polymers grafted wholly or partly with the monomers i), ii) and optionally iii),
   v) optionally, in the presence of a non radical crosslinking agent, having in its single molecule two or more functional groups each of which allows formation of an ester or an amide bond by reaction with carboxyl groups;
b) drying and optionally grinding and/or sifting the material of step a) to obtain base water-absorbing polymeric particles;
c) subsequent post-crosslinking of said base particles obtained from the polymerization step b);
d) optionally coating said post-crosslinked particles of step c), with any of the coating agents described below as additional coating agents;
e) vacuum treating and optionally plasma treating said particles of step c) or d).

Alternatively, the process above entails steps a), b) and c) and then step e), and then the subsequent coating step d), so that coating takes place after vacuum and optional plasma treatment.

Alternatively, the coating step d) takes place prior to post-crosslinking step c).

In some embodiments herein, the water-absorbing polymers particles of the present invention are produced by
a) polymerization of a monomer solution comprising
   i) at least one ethylenically unsaturated acid functional monomer,
   ii) at least one ethylenically unsaturated crosslinker,
   iii) optionally one or more ethylenically and/or allylically unsaturated monomers copolymerizable with i),
   iv) optionally one or more water-soluble polymers grafted wholly or partly with the monomers i), ii) and optionally iii),
   v) optionally in the presence of a non radical crosslinking agent, having in its single molecule two or more functional groups each of which allows formation of an ester or an amide bond by reaction with carboxyl groups.
b) drying, grinding, sifting and subsequent post-crosslinking of the hydrogels obtained from the polymerization step a),
c) coating, before, during or after post-crosslinking with at least one film forming polymer for example selected from polyurethanes and polyacrylates, and are optionally heat treated after coating at a temperature between 40-190° C. for a time period between 0-90 minutes,
d) vacuum treatment of the post-crosslinked water absorbing polymeric particles, and
e) optionally, plasma treatment prior, during or after execution of step d).

In some embodiments herein, the water-absorbing polymers particles of the present invention are produced by:
a) polymerization of a monomer solution comprising:
   i) at least one ethylenically unsaturated acid functional monomer,
   ii) at least one ethylenically unsaturated crosslinker,
   iii) optionally one or more ethylenically and/or allylically unsaturated monomers copolymerizable with i),
   vi) optionally one or more water-soluble polymers grafted wholly or partly with the monomers i), ii) and optionally iii),
   v) optionally in the presence of a non radical crosslinking agent, having in its single molecule two or more functional groups each of which allows formation of an ester or an amide bond by reaction with carboxyl groups.
b) drying, grinding, sifting and subsequent post-crosslinking of the hydrogels obtained from the polymerization step a),
c) coating, before, during or after post-crosslinking, with at least one inorganic permeability enhancing agent for example selected from water-insoluble metal phosphates, inorganic particles for example silica, clay, or mica, which can be applied as powders or as aqueous dispersions,
d) vacuum treatment of the post-crosslinked water absorbing polymeric particles, and
e) optionally, plasma treatment prior, during or after execution of step d).

In some embodiment herein, the water-absorbing polymers particles of the present invention are produced by:

a) polymerization of a monomer solution comprising
   i) at least one ethylenically unsaturated acid functional monomer,
   ii) at least one ethylenically unsaturated crosslinker,
   iii) optionally one or more ethylenically and/or allylically unsaturated monomers copolymerizable with i),
   vi) optionally one or more water-soluble polymers grafted wholly or partly with the monomers i), ii) and optionally iii),
   v) optionally in the presence of a non radical crosslinking agent, having in its single molecule two or more functional groups each of which allows formation of an ester or an amide bond by reaction with carboxyl groups;
b) drying, grinding, sifting and subsequent post-crosslinking of the hydrogels obtained from the polymerization step a),
c) coating, before, during or after post-crosslinking with at least one inorganic permeability enhancing agent for example selected from water-insoluble metal phosphates, inorganic particles for example silica, clay, or mica, which can be applied as powders or as aqueous dispersions, and/or at least one water soluble polyvalent metal salt, for example selected from aluminum lactate, zirconium lactate, aluminum sulfate, zirconium sulfate, (and that may be are coated) before, during or after post-crosslinking with at least one film forming polymer for example selected from polyurethanes and polyacrylates, and are optionally heat treated after coating at a temperature between 40-190° C. for a time period between 0-90 minutes),
d) vacuum treatment of the post-crosslinked water absorbing polymeric particles, and
e) optionally, plasma treatment prior, during or after execution of step d).

In some embodiments herein, the method of producing water-absorbing particles comprises the step of treating the surface-cross-linked (and optionally coated) water-absorbing particles with water and/or a water-miscible organic solvents prior to vacuum- and/or prior to plasma treatment.

For example, the surface-crosslinked (and optionally coated) water-absorbing particles are treated with 0.1 to 5% (by weight of the water-absorbing particles) with water and/or a water miscible-organic solvent. Suitable water-miscible organic solvent are for example aliphatic $C_1$-$C_4$-alcohols, such as methanol, i-propanol and t-butanol, polyhydric alcohols, such as ethylene glycol, 1,2-propanediol and glycerol, ethers, such as methyltriglycol and polyethylene glycols having average molecular weight $M_w$ of 200-10 000 and also ketones such as acetone and 2-butanone.

Optional: Coating with Coating Agents

In addition to the treatment with plasma and/or vacuum, the (e.g. base) water-absorbing polymeric particles or the post-crosslinked water-absorbing polymeric particles may be coated with coating agents; such material is herein referred to as coated post-crosslinked water-absorbent polymeric particles, and coated post-crosslinked water-absorbing polymeric particles.

The coating may be done before, during or after post-crosslinking. In one embodiment, the coating takes place after post-crosslinking.

The coating step may for example be done with apparatuses described above for the post-crosslinking. It may for example be done in the same step as the post-crosslinking.

Such coating with one or more coating agent(s) makes it possible to achieve additional effects, such as a reduced tendency to cake, improved processing properties or a further enhanced Saline Flow Conductivity (SFC).

"Coating" when used herein includes partial coatings, whereby the outer surface of the particles are partially covered with a coating agent, homogeneous coatings, whereby the coating is present in a homogeneous amount per surface area of the particle, complete coatings, whereby substantially the complete surface of the particles is covered (and for example homogeneously) or whereby said coating agent forms a substantially complete network on said surface of said particles (and for example homogeneously), and homogeneous complete coatings.

The coating agent may be or may comprise a hydrolyzed pre-cursor of polyvinylamine, polyethyleneimines, polyallylamines. The coating agent may be or comprise a metal phosphates, inorganic particles, and water soluble polyvalent metal salts.

In a particular embodiment polyvalent metal salts, most preferably water soluble polyvalent metal salts, like for example but not limited to aluminum sulfate, aluminum nitrate, aluminum chloride, potassium aluminum sulfate, sodium aluminum sulfate, magnesium sulfate, magnesium citrate, magnesium lactate, zirconium sulfate, zirconium lactate, iron lactate, iron citrate, calcium acetate, calcium propionate, calcium citrate, calcium lactate, strontium lactate, zinc lactate, zinc sulfate, zinc citrate, aluminum lactate, aluminum acetate, aluminum formiate, calcium formiate, strontium formiate, strontium acetate may be used as or in said coating agent, e.g. to impart a high passive fluid transport (SFC) by homogeneously coating the surface of the water-absorbing polymeric particles prior to, during or after post-cross-linking. It should be understood that such polyvalent metal salts are sued in addition to the post-crosslinkers, described herein.

(It may be that the coating agent is or comprises water soluble polyvalent metal salt, preferably selected from aluminumlactate, zirconiumlactate, aluminumsulfate, zirconiumsulfate.)

The coating agent may be selected from water-insoluble metal phosphates and other inorganic particles, for example silica, clay, or mica, which can be applied as powders or as aqueous dispersions.

In one embodiment, the particles comprise at least a coating of silica, such as commercially available Aerosil (ex BASF). Silica is known in the art to improve the absorption speed of the water-absorbent polymer particles. The inventors found that when silica is used on water-absorbent polymer particles as known in the art, the permeability may be negatively affected, e.g. SFC may be reduced. Surprisingly, the inventors found that when silica is used as a coating agent for the vacuum-treated post-crosslinked water-absorbent polymer particles of the invention, that are treated with a vacuum and optionally said plasma treatment step, the permeability is not reduced by the addition of said silica, whilst the FHA is improved.

Suitable water-insoluble metal phosphates are for example phosphates which can be deemed to be "phosphates" in the technical sense, such as phosphate oxides, phosphate hydroxides, phosphate silicates, phosphate fluorides or the like. As used herein, the term "water-insoluble" denotes a solubility of less than 10 g, e.g. of less than 1 g and more preferably less than 0.1 g in 1000 ml of water at 25° C. Suitable water-insoluble metal phosphates and suitable coating processes are described in WO 02/060983 which is expressly incorporated in here by reference. Suitable water-insoluble metal phosphates are pyrophosphates, hydrogen phosphates and phosphates of calcium, of magnesium, of strontium, of barium, of zinc, of iron, of aluminum, of titanium, of zirconium, of hafnium, of tin, of cerium, of scandium, of yttrium or of lanthanum, and also mixtures thereof. Suitable water-insoluble metal phosphates are calcium hydrogenphosphate, calcium phosphate, apatite, Thomas flour, berlinite ($AlPO_4$) and Rhenania phosphate. Particular preference may for example be given to calcium hydrogenphosphate, calcium phosphate and apatite, the term "apatite" denoting fluoroapatite, hydroxyl apatite, chloroapatite, carbonate apatite and carbonate fluoroapatite. It will be appreciated that mixtures of various water-insoluble metal phosphates can be used.

The water-insoluble metal phosphates may have an average particle size of usually less than 400 µm, preferably less than 100 µm, for example less than 50 µm, or for example in the range of 2 to 20 µm.

The fraction of water-insoluble metal phosphate is usually in the range from 0.1% to 1.0% by weight, for example in the range from 0.2% to 0.8% by weight, based on the water-absorbing polymeric particles.

But it is also possible for the water-insoluble metal phosphates to be formed in situ on the surface of the base or post-crosslinked water-absorbing polymeric particles. To this end, solutions of phosphoric acid or of soluble phosphates and solutions of soluble metal salts are separately sprayed on, the water-insoluble metal phosphate forming and depositing on the particle surface.

Suitable inorganic particles may be applied as powders or aqueous dispersions. Examples but not limited to are silica, fumed silica, colloidal dispersed silica, titaniumdioxide, aluminum- and magnesiumoxide, zinc oxide, clay. Silicas may be hydrophilic or hydrophobic.

Hydrophilic silicas, such as Aerosils, may be used to make the particles more hydrophilic. However, the inventors found that in some embodiments herein, whereby the absorbent structure comprises adhesive, in particular when it comprises thermoplastic adhesive material, such inorganic particles, in particular silicas, may have a negative impact on the absorbent structure's performance.

Some of the coating agents, in particular the polymeric coating agents described herein may render the absorbent structures with the articles more permeable for liquid, increasing thus the SFC of the structure and of the particles, which is highly desirable, but it is believed that they may render the post-crosslinked water-absorbent polymeric particles less hydrophilic. Without wishing to be bound by theory it is understood that a less hydrophilic surface of the water-absorbing polymeric particles typically reduces the FSR and the FHA comes with a much improved SFC. Thus, for such coated particles herein, said surface treatment with vacuum and/or plasma, as described herein, is particular beneficial.

Coating may for example be done before, or (in one embodiment preferably) during or after post-crosslinking, with a coating agent selected from: film-forming polymers and/or elastic polymers and/or elastic film-forming polymers. Such coating agents may be applied so that they form complete coatings, and for example homogeneous and complete coatings. They may for example be sprayed on. When the coating agent is sprayed in the form of dispersions, they are for example used as aqueous dispersions. When applied as a dispersion, the coating agents that are elastic and/or film-forming polymers may be annealed.

Suitable film-forming polymers may exhibit elastic physical properties. The elastic and elastic film-forming agents/polymers suitable as coating agents herein are disclosed in U.S. Pat. No. 5,731,365 and in EP 0703265, and also in WO 2006/082242 and WO 2006/097389. In one embodiment the elastic and/or film-forming polymer coating agent is selected from polyurethanes, poly(meth)acrylates, which optionally can be cross-linked by e.g. Zn, polyacrylates, and copolymers of styrene-(meth)acrylate, and copolymers of styrene and/or (meth)acrylate comprising acrylonitrile, copolymers of butadiene-styrene and/or acrylonitrile, (co)polymers of (cross-linkable) N-Vinylpyrrolidone and (co)polymers of vinylacetate and mixtures thereof.

The elastic and or film-forming polymer may be applied as aqueous dispersion and optionally coalescing agents and/or anti-oxidants may be added.

If the elastic and/or film-forming polymer is present, it may for example be present in an amount up to 5 wt. %, or up to 1.5 wt. %, or up to 0.5 wt. %, or for example from 0.01 wt. %, based on the post-crosslinked water-absorbing polymer.

The elastic and/or film-forming polymer herein include single polymers and blends of polymers. 'Film-forming' means that the respective polymer can readily be made into a film, i.e. layer or coating, e.g. a homogeneous coating on the particle, upon evaporation of the solvent in which it is dissolved or dispersed. The polymer may for example be thermoplastic or crosslinked.

'Elastic' when used herein means that the material will exhibit stress induced deformation that is partially or completely reversed upon removal of the stress.

'Phase-separating', when used herein, means that a film of the polymeric coating agent (i.e. prior to use in or as the coating agent and application to the particles) has at least two distinct spacial phases which are distinct and separated from one another, due to their thermodynamic incompatibility. The incompatible phases are comprised of aggregates of only one type of repeat unit or segment of the elastic material. This can for example occur when the polymer is a block (or segmented) copolymer, or a blend of two immiscible polymers, e.g. a elastic and/or a film-forming block (or segmented) copolymer, or blend of immiscible polymers. The phenomenon of phase separation is for example described in: Thermoplastic Elastomers: A Comprehensive Review, eds. Legge, N. R., Holden, G., Schroeder, H. E., 1987, Chapter 2.

Typically, the phase separation occurs in a block copolymer, whereby the segment or block of the copolymer that has a Tg below room temperature (i.e. below 25° C.) is said to be the soft segment or soft block and the segment or block of the copolymer that has a Tg above room temperature is said to be the hard segment or hard block.

The Tg's, as referred to herein, may be measured by Differential Scanning calorimetry (DSC) to measure the change in specific heat that a material undergoes upon heating. The DSC measures the energy required to maintain the temperature of a sample to be the same as the temperature of the inert reference material (eg. Indium). A Tg is determined from the midpoint of the endothermic change in the slope of the baseline. The Tg values are reported from the second heating cycle so that any residual solvent in the sample is removed.

In addition, the phase separation can also be visualised by electron microscopy particularly if one phase can be stained preferentially. Also atomic force microscopy has been described as a particularly useful technique to characterize the morphology (phase-separating behavior) of the preferred thermoplastic polyurethanes, described herein after.

The elastic (e.g. film-forming) polymer herein may comprise at least two phases with different glass transition temperatures (Tg); it comprises for example at least a first phase with a $Tg_1$, which is lower than the $Tg_2$ of a second phase, the difference being at least 30° C.

In one embodiment, the elastic polymer has a first (soft) phase with a $Tg_1$ which is less than 25° C., preferably less than 20° C., more preferably less than 0° C., or even less than −20° C., and a second (hard) phase with a $Tg_2$ of at least 50° C. or even at least 55° C., but more preferably more than 60° C. or even more than 70° C., or in certain embodiments, more than 100° C., provided the temperature difference between $Tg_1$ and $Tg_2$ is at least 30° C., preferably at least 50° C. or even at least 60° C., or in certain embodiments at least 90° C.

It should be understood that, the coating agent itself (i.e. before formation into the coating on the particles) has the herein specified properties, but that that typically, the coating material maintains these properties once in the coating, and that the resulting (film of the) coating should thus preferably have the same properties.

Polymers having film-forming and also elastic properties are generally suitable, such as copolyesters, copolyamides, polyolefins, styrenic block copolymers, including styrene-isoprene block copolymers, styrene-butadiene block copolymers, and polyurethanes, and blends thereof, optionally blends including at least polyurethanes. Some include polyurethanes and polyurethane blends.

Polyurethanes useful herein may include one or more phase-separating block copolymers, having a weight average molecular weight Mw of at least 5 kg/mol, and may be at least 10 kg/mol and higher. In one embodiment such a block copolymer has at least a first polymerized homopolymer segment (block) and a second polymerized homopolymer segment (block), polymerized with one another, whereby the first (soft) segment may have a Tg1 of less than 25° C. or even less than 20° C., or even less than 0° C., and the second (hard) segment has a Tg2 of at least 50° C., or of 55° C. or more, and may be 60° C. or more or even 70° C. or more.

In another embodiment, such a block copolymer has at least a first polymerized polymer segment (block) and a second polymerized polymer segment (block), polymerized with one another, whereby the first (soft) segment may have a Tg1 of less than 25° C. or even less than 20° C., or even less than 0° C., and the second (hard) segment has a Tg2 of at least 50° C., or of 55° C. or more, may be 60° C. or more or even 70° C. or more.

The weight average molecular weight of a first (soft) segment (with a Tg of less than 25° C.) may be at least 500 g/mol, at least 1000 g/mol or even at least 2000 g/mol, and maybe less than 8000 g/mol, and may be less than 5000 g/mol.

However, the total of the first (soft) segments may be 20% to 95% by weight of the total block copolymer, or even from 20% to 85% or may be from 30% to 75% or even from 40% to 70% by weight. Furthermore, when the total weight level of soft segments is more than 70%, it may be that an individual soft segment has a weight average molecular weight of less than 5000 g/mol.

The elastic and/or film-forming polymer is typically such that at least some of the resulting coating on the water-absorbent polymers herein is not water-soluble and, optionally not water-dispersible once a coating has been formed.

In one embodiment, the hydrophobic film-forming polymer has a minimum film-forming temperature above −10° C., preferably above 20° C., more preferably above 50° C., and most preferably above 80° C.

The polymers herein, such as the polyurethanes herein, can be applied to the post-crosslinked or base water-absorbing polymeric particles as a solution or as a dispersion. Some may be aqueous dispersions, further described below. The solution can be prepared using any suitable organic solvent for example acetone, isopropanol, tetrahydrofuran, methyl ethyl ketone, dimethyl sulfoxide, dimethylformamide, N-methylpyrrolidone, chloroform, ethanol, methanol or mixtures thereof.

Suitable elastic and e.g. film-forming polymers which are applicable from solution are for example Vector® 4211 (Dexco Polymers, Texas, USA), Vector 4111, Septon 2063 (Septon Company of America, A Kuraray Group Company), Septon 2007, Estane® 58245 (Noveon, Cleveland, USA), Estane 4988, Estane 4986, Estane® X-1007, Estane T5410, Irogran PS370-201 (Huntsman Polyurethanes), Irogran VP 654/5, Pellethane 2103-70A (Dow Chemical Company), Elastollan® LP 9109 (Elastogran).

Some aqueous polyurethane dispersions are Hauthane HD-4638 (ex Hauthaway), Hydrolar® HC 269 (COIMolm, Italy), Impraperm® 48180 (Bayer Material Science AG, Germany), Lurapret® DPS (BASF Aktiengesellschaft, Germany), Astacin® Finish LD 1603 (BASF Aktiengesellschaft, Germany), Permax® 120, Permax 200, and Permax 220 (Noveon, Brecksville, Ohio), Syntegra YM2000 and Syntegra YM2100 (Dow, Midland, Mich.), Witcobond® G-213, Witcobond G-506, Witcobond G-507, Witcobond 736 (Uniroyal Chemical, Middlebury, Conn.), Astacin Finish PUMN TF, Astacin TOP 140, Astacin Finish SUSI (all BASF) and Impranil® DLF (anionic aliphatic polyester-polyurethane dispersion from Bayer Material Science).

The coating polymer, e.g. polyurethane, may be hydrophilic and in particular surface hydrophilic. This hydrophilicity may be achieved or enhanced via addition of fillers, surfactants, deagglomeration and coalescing agents. In another embodiment, the hydrophilic properties are (in addition) achieved as a result of the polyurethane including hydrophilic polymer blocks, for example polyether groups having a fraction of groups derived from ethylene glycol (CH2CH2O) or from 1,4-butanediol (CH2CH2CH2CH2O) or from 1,3-propanediol (CH2CH2CH2O) or from 1,2-propanediol (—CH(CH3)-CH2O—), or mixtures thereof.

It is further possible to obtain hydrophilic properties for the polyurethanes through an elevated fraction of ionic groups, and may be carboxylate, sulfonate, phosphonate or ammonium groups. The ammonium groups may be protonated or alkylated tertiary or quarternary groups. Carboxylates, sulfonates, and phosphates may be present as alkali-metal or ammonium salts. Suitable ionic groups and their respective precursors are for example described in "Ullmanns Encyclopädie der technischen Chemie", 4th Edition, Volume 19, p. 311-313 and are furthermore described in DE-A 1 495 745 and WO 03/050156.

It may be useful to apply the coating in a fluidized bed reactor. The base or post-crosslinked water-absorbing particles are introduced as generally customary, depending on the type of the reactor, and are generally coated by spraying with the elastic and/or film-forming polymer as a solid material or may be as a polymeric solution or dispersion. Aqueous dispersions of the elastic and or film-forming polymer may be used for this.

The concentration of elastic and/or film-forming polymer in the solution or dispersion may be in the range from 1% to 60% by weight, may be in the range from 5% to 40% by weight and may be in the range from 10% to 30% by weight.

The resulting coated particles may be annealed. This optional annealing step c) typically involves a step resulting in a further strengthened or more continuous or more completely connected coating and it substantially eliminates defects, e.g. annealing the coating agent (e.g. annealing and thereby connecting the coating agent particles in a dispersion, to form a coating).

Typically, the annealing step) involves a heat treatment of the particles with a coating of said coating agent; it may be done by for example radiation heating, oven heating, convection heating, azeotropic heating, and it may for example take place in conventional equipment used for drying, such as fluidized bed driers.

The annealing step may involve heating the coated (post-crosslinked) water-absorbing polymers at a temperature which is above the highest Tg of the coating agent, preferably to a temperature which is at least 20° C. above said highest Tg.

For example, the highest Tg is typically at least 50° C. and the annealing temperature is at least 70° C., or even at least 100° C. or even at least 140° C., and up to 200° C. or even up to 250° C.

If the material has a melting temperature Tm, then the annealing step is at least 20° C. below the Tm and if possible and for example at least 20° C. or at least 50° C. above the highest Tg.

The annealing step may be done for, for example, at least 5 minutes, or even for at least 10 minutes or even for at least 15 minutes, or even at least 30 minutes or even at least 1 hour or even at least 2 hours.

This heat-treatment may be done once, or it may be repeated, for example the heat treatment may be repeated with different temperatures, for example first at a lower temperature, for example from 70° C. or 80° C., to 100° C., as described above, for example for at least 30 minutes or even 1 hour, up to 12 hours, and subsequently at a higher temperature, for example from 120° C. to 140° C., for at least 10 minutes.

During the annealing step, the coated water-absorbent polymers may also be dried at the same time.

The coated post-crosslinked water-absorbing polymeric particles or vacuum-treated coated post-crosslinked water-absorbing polymeric particles herein may have CCRC values that are as the CRC values cited above for the post-crosslinked or vacuum-treated post-crosslinked water-absorbent polymeric particle, respectively, when the coating agent is one of the elastomeric and/or film-forming polymeric materials above.

The coated post-crosslinked water-absorbing polymeric particles or vacuum-treated coated post-crosslinked water-absorbing polymeric particles herein may have CS-SFC values that are as the SFC values cited above for the post-crosslinked or vacuum-treated post-crosslinked water-absorbent polymeric particle, respectively, when the coating agent is one of the elastomeric and/or film-forming polymeric materials above.

The coated post-crosslinked water-absorbing polymeric particles or vacuum-treated coated post-crosslinked water-absorbing polymeric particles herein may have CS-AUL values that are as the AUL values cited above for the post-crosslinked or vacuum-treated post-crosslinked water-absorbent polymeric particle, respectively, when the coating agent is one of the elastomeric and/or film-forming polymeric materials above.

Absorbent Structures

The absorbent structure herein may be an acquisition layer of an absorbent article, that serves to absorb and distribute a liquid; in one preferred embodiment herein, the absorbent structure herein is an absorbent core of an absorbent article, said core comprising, e.g. at least one layer of the core that comprises, said vacuum-treated post-crosslinked water-absorbing polymeric particles. The absorbent structure is typically for use in an absorbent article, such as a diaper or feminine hygiene article.

The absorbent structure may also have a multitude of layers, e.g. more than one, for example two or three layers, superimposed on one another in the plane of the article, each comprising the vacuum treated post-crosslinked polymeric particles.

The absorbent structure has a Z-direction thickness, and a width (X-direction) and length (Y-direction), said x-y direction being in the plane of the structure/absorbent article.

The absorbent structure has typically a surface area (X-Y plane) of at least 4 cm2, or at least 10 cm2 or at least 20 cm2. In one embodiment, the absorbent structure includes at least 1 gram of the vacuum treated post-crosslinked water-absorbing polymeric particles, or at least 3 grams or at least 5 grams. The absorbent structure may have for example a volume of at least 1 $cm^3$, or at least 5 $cm^3$ or at least 10 $cm^3$ (when laid out flat, under normal atmospheric pressure, conditioned for 24 hrs at 20° C., 50% relative humidity).

In one embodiment, the absorbent structure is substantially free or free of absorbent cellulosic fibers. To immobilise and/or structure the vacuum treated post-crosslinked water-absorbing polymeric particles in said absorbent structure, the absorbent structure may comprise a structuring and/or immobilisation aid. This may be a non-absorbing (e.g. less than 5 g/g) material.

This may be a thermoplastic material (polymer), adhesive material (polymer) and/or thermoplastic adhesive material (polymer), that may be fibrous, and that may be non-absorbing.

The thermoplastic adhesive component may be present at a level of for example 0.5% to 50% by weight of the absorbent structure, or from 1.0% or from 1.5% or from 3% or from 5% or from 7% to 35% or to 30% or to 20% or to 15% by weight of the absorbent structure.

A thermoplastic adhesive herein may for example have a viscosity of between 800 and 4000 mPa·s, or from 1000 mPa·s or 1200 mPa·s or from 1600 mPa·s to 3200 mPa·s or to 3000 mPa·s or to 2800 mPa·s or to 2500 mPa·s, at 175° C., as measurable by ASTM D3236-88, using spindle 27, 20 pmp, 20 minutes preheating at the temperature, and stirring for 10 min.

The thermoplastic adhesive may for example have a softening point of a temperature between 60° C. and 150° C., between 75° C. and 135° C., or between 90° C. and 130° C., or between 100° C. and 115° C., as can be determined with ASTM E28-99 (Herzog method; using glycerine).

In one embodiment herein, the thermoplastic adhesive component may be hydrophilic, having a contact angle of less than 90°, or less than 80° or less than 75° or les than 70°, as measurable with ASTM D 5725-99.

The thermoplastic adhesive component may include thermoplastic polymers, e.g. of a weight average molecular weight of at least 8000, or at least 12,000, or at least 15,000 (g/mole).

Some are thermoplastic polymers, co-polymers or block co-polymers with a polyolefin, polyether, polyester and/or polyamide units.

Example polymers include ethylene vinyl acetate polymers (EVA), the vinyl acetate is generally in the range of 15-40 weight %, or amorphous poly-alpha olefin (APAO). Further exemplary polymers are (styrenic) block copolymers (SBC), including A-B-A triblock structures, A-B diblock structures and (A-B)n radial block copolymer structures wherein the A blocks are non-elastic polymer blocks, typically including polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. The thermoplastic polymer may include a styrene-isoprene-styrene (SIS), and/ or a styrene-butadiene-styrene (SBS) and/or styrene-ethylene/butylene-styrene (SEBS), or may be SIS. The triblock may for example consist of about 14-22 weight % styrene for SIS copolymers and above 25 weight % styrene for SBS copolymers. Triblock can also contain 0-50 weight % of diblock.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alphaolefins, for example of propene-ethylene, propene-butene, propene-hexene, or terpolymers of propene-butene-ethene made by a Ziegler-Natta polymerization.

The adhesive comprising thermoplastic polymers may comprise a plasticizers, such as an oil and/or a waxes; it may however be preferred that (the more hydrophilic) esters of oils and fats are used as plasticiser(s), including glycerol esters of fatty acids (e.g. derived from fat or oil), or such polymerised compounds, or for example PureSyn (PureSyn 3E20) esters.

Some exemplary plasticizers include: polyethylene glycols (PEG's), polypropylene glycol (PPG's), alcohol ethoxylates, and/or any derivatives thereof; for example polyethylene glycol, polypropylene glycol, alcohol ethoxylates, and/or any derivatives thereof of a MW of below 1000, for example, PEG 400 used (which is (at 20° C.) a liquid, with MW=400 (on average)). The thermoplastic adhesive component may comprise a polyethylene glycol, polypropylene glycol, alcohol ethoxylates, and/or any derivatives thereof of a MW of at least 1000, for example PEG 10000 may be used (which is (at 20° C.) a solid, with MW=10,000 (and MW is between 8500-11500)); it may comprise a long chain ethoxylated alcohol such as Unitox Ethoxylate 420 or 450, or a glycerin, glycerol, sorbitol, or ester compound, including citric acid esters may be useful as plasticizer. The plasticizer may alternatively, or in addition, comprise a polyalphaolefins (hydrogenated) synthetic hydrocarbon plasticizer, e.g. provided of average Molecular weight of 1000 or more (such as Durasyn 180; being of average MW=2000). Also useful plasticizers include branched polyalkanes or branched polyalkenes, such as branched butane hydrocarbon polymers, e.g., of Mw of 1000 or more, including for example Indopol H-6000 of weight average MW=7560, and alternatively Indopol H-15.

In one embodiment, the thermoplastic adhesive component includes a plasticizer that has have a weight average Mw (in gram/mole) of at least 1000, or at least 2000, or at least 3000 or at least 3500, or at least 4000, or at least 5500; and its weight average molecular weight may be less than 15,000 or less than 12,000, or up to 8000 (g/mole). Then, the thermoplastic adhesive component may be free of plasticizers of a weight average molecular weight below 1000 g/mole, or below 2000 g/mole.

A typical level of the plasticizer is from 0.5 to 50%, or 1% to 45% or 5% to 45%, or 10% to 40% by weight of the thermoplastic adhesive component.

A tackifying agent may be included in the thermoplastic adhesive component, as known in the art. In one embodiment, the tackifying agent has a weight average molecular weight of at least 1000, or at least 2000 or at least 3000 or at least 4000. It may be a material that is solid at 20° C. In one embodiment, the thermoplastic adhesive component is substantially free of tackifying agents of a weight average molecular weight below 1000.

Alternatively, or in addition, the tackifying agent may be hydrophilic, and/or water-dispersible and/or water-soluble, for example water-soluble, having for example a water-solubility of at least 30% or at least 40% or at least 50%, as defined by the method described herein below.

Suitable tackifying agents include: rosin, rosin derivatives, including rosin esters.

Typical concentrations (levels) of the tackifying agent in the thermoplastic adhesive component are in the range of from 7% or from 10% or from 20% or from 30%, to 70% or to 60% or to 50% by weight of the component.

The thermoplastic adhesive component may be such that it can be fiberized, and it may be that it is present in the absorbent layer in the forms of fibers, i.e. the thermoplastic adhesive component is fiberized or fibrous. It may be that it forms a fibrous matrix for the vacuum-treated water-absorbing polymeric particles.

The thermoplastic adhesive fibers may have an average thickness of 1-50 micrometer and an average length of 5 mm to 50 cm.

The absorbent structure typically comprises one or more substrate to support said vacuum-treated post-crosslinked water-absorbing polymeric particles, typically said one or more substrates enclosing together said particles.

In one embodiment the absorbent substructure comprises at least 50% by weight of said absorbent structure of said vacuum-treated post-crosslinked water-absorbent polymeric particles.

In one embodiment herein, the absorbent structure is an absorbent core of an absorbent article, comprising one or more core substrate material (or: covering materials), enclosing an interior volume comprising absorbent material and optional further materials, whereby said vacuum-treated post-crosslinked water-absorbent polymeric particles are present at a level of at least 65%, or at least 75% or at least 90% by total weight of said absorbent material and optional further materials, said optional further materials may be present and including (non-absorbing) thermoplastic polymers, e.g. in fibrous form, and/or adhesive material, e.g. in fibrous form, and/or thermoplastic adhesive polymers.

The vacuum-treated post-crosslinked water-absorbing polymeric particles and said thermoplastic polymer, and/or adhesive polymer, and/or thermoplastic adhesive polymer may form together at least 75%, or at least 90% by weight of the absorbent structure.

In one embodiment, the absorbent structure may comprise said non-absorbent immobilisation/structuring aid and said vacuum-treated post-crosslinked water-absorbing polymeric particles in a weight ratio of from 1:1, or from 1:2 or from 1:3, to 1:40 or to 1:30 or to 1:20 or to 1:15.

The absorbent structure can be made by any method known in the art. For example, the particles may be transferred to a substrate, and then optional materials may be added, and then a further substrate may be added, and attached to the first substrate, or the first substrate may be folded over the particles and sealed to itself. In one embodiment, the particles are deposited on a substrate by an indirect printing method. In one embodiment, this may be done with a print roll, that comprises rows and columns of cavities that are filled with said particles, and then rotates towards a moving substrate, where on the particles are deposited (in rows and columns of particles). Said substrate may comprise an adhesive material or component, e.g. as described herein.

The immobilisation/structuring aid may then be added onto the substrate and/or onto the particles; for example at least or only onto said particles.

When including the thermoplastic and/or adhesive material, is present in the form of fibers and the process to make the absorbent layer involved fiberizing the thermoplastic adhesive component. The structuring/immobilisation aid may be applied by spraying it in liquid form onto the vacuum-treated post-crosslinked water-absorbing polymeric particles, for example by use of spray nozzle(s).

The substrate sheet (or covering sheet) of the absorbent structure herein may be any material, e.g. layer or sheet, capable to hold, or support or contain particles herein. Typically, it is a web or sheet material, such as a film, woven web and/or nonwoven web, as known in the art. In one embodiment it is a nonwoven sheet. The substrate may for example include spunbond, meltblown and/or carded nonwovens. The substrate may be a so-called SMS material or SMMS material, including a spunbond layer, one or two, respectively, melt-blown layers and a further spunbond layer. It may be a permanently hydrophilic nonwoven, and/or a nonwoven with hydrophilic coating. Some nonwoven materials are provided from synthetic fibers, such as polyethylene, PET and may be polypropylene. As the polymers used for nonwoven production may inherently be hydrophobic, they may be coated with hydrophilic coatings, e.g., coated with nanoparticles, as known in the art. Nonwoven materials and absorbent structures using such materials are described in, for example, co-pending applications US 2004/0162536, EP1403419-A, WO2002/0192366, EP1470281-A and EP1470282-A.

The substrate may enclose the internal volume of the absorbent structure (including or being said vacuum-treated post-crosslinked water-absorbing polymeric particles) or only cover one side of the structure, and then one or more further covering materials (further substrates/coversheets) may be used to enclose said internal volume (e.g. including or being said particles).

Absorbent structure for use in absorbent articles herein may include a substrate material sheet and thereon one or more layers of the vacuum-treated post-crosslinked water-absorbent polymeric particles.

The vacuum-treated post-crosslinked water-absorbing polymeric particles and said non-absorbing immobilisation/structuring aid may be present as separate layer or layers, or they may be present, mixed together, as one or more mixed layers. Thereby, the immobilisation/structuring aid can form a matrix, e.g. cavities or network, for said particles e.g. to hold them in the cavities or network.

An absorbent structure herein can for example be made as follows:
a) providing one or more substrate sheet materials (together forming the substrate, as referred to herein), e.g. that can serve as a covering or partial covering material;
b) providing vacuum-treated post-crosslinked water-absorbing polymeric particles;
c) providing a immobilizing/structuring aid, e.g. a thermoplastic adhesive component, as described herein;
and then forming a water-absorbent structure by either:
d i) depositing said aid, e.g. said thermoplastic adhesive component, on the substrate sheet material and then the vacuum treated (optionally coated) post-crosslinked water-absorbing polymeric particles onto the thermoplastic adhesive component; and/or
d ii) depositing the vacuum-treated post-crosslinked water-absorbent polymeric particles on the substrate sheet material and then said aid, e.g. said thermoplastic adhesive component onto the vacuum-treated water-absorbent polymeric particles; and/or
d iii) mixing said aid, e.g. said thermoplastic adhesive component, and said vacuum-treated post-crosslinked water-absorbent polymeric particles and then depositing the mixture on the substrate sheet material;
and then:
e) enclosing the resulting component with the substrate sheet material(s) and typically sealing the substrate sheet material; or
h) repeating steps a) to d) to obtain two or more absorbent components which are then combined to form the final absorbent component, and then applying step g) above, to obtain the absorbent structure, typically by ensuring the substrate sheet materials of each component form one of the outer surfaces of the absorbent structure.

Optionally, the vacuum-treated post-crosslinked water-absorbent polymeric particles and/or the immobilisation/structuring aid, e.g. the thermoplastic adhesive component, and/or the mixture thereof may be applied in a pattern, e.g. with varying dimensions, e.g. thickness, width or length, and/or in a pattern, whereby the absorbent structure includes at least one zone (e.g. of at least 1×1 mm) which is substantially free of one or more of these compounds.

The absorbent articles herein may have typically a topsheet and a backsheet, which each have a front region, back region and crotch region, positioned therein between, each being one third of the length of the article, and the full width of the article. The absorbent structure, as described herein is typically positioned in between the topsheet and backsheet. Some suitable backsheets are vapor pervious but liquid impervious. Some suitable topsheet materials may be at least partially hydrophilic; alternatively, or in addition, the topsheet may be a so-called apertured topsheet, including apertured formed films, as known in the art. It may be that the topsheet includes a skin care composition, e.g. a lotion composition.

The backsheet may be liquid impervious, as known in the art. In some preferred embodiments, the liquid impervious backsheet comprises a thin plastic film such as a thermoplastic film having a thickness of about 0.01 mm to about 0.05 mm. Suitable backsheet materials comprise typically breathable material, which permit vapors to escape from the diaper while still preventing exudates from passing through the backsheet. Suitable backsheet films include those manufactured by Tredegar Industries Inc. of Terre Haute, Ind. and sold under the trade names X15306, X10962 and X10964.

The backsheet, or any portion thereof, may be elastically extendable in one or more directions. The backsheet may be attached or joined to a topsheet, the absorbent core, or any other element of the diaper by any attachment means known in the art. It may be that the longitudinal side edges of the topsheet and backsheet are directly attached to one another, but that the longitudinal edges of the topsheet and the core are not attached to one another.

The absorbent structure may have the full length of the absorbent article, or only part thereof. It may for example typically be present in at least the crotch region, or for example also in the front waist region, and for example in part of the back waist region.

The infant diapers may for example have an average caliper in the crotch region of less than 1.0 cm, less than 0.7 cm, less than 0.5 cm, or even less than 0.3 cm (for this purpose alone, the crotch region being defined as the central zone of the product, when laid out flat and stretched, having a dimension of 20% of the length of the article and 50% of the width of the article).

Some articles herein have a relatively narrow crotch width, such as a crotch width of less than 100 mm, 90 mm, 80 mm, 70 mm, 60 mm or even less than 50 mm, as measured along a transversal line, which is positioned at equal distance to the front edge and the rear edge of the article.

The diaper herein may have pre-fastened waist regions (or band thereof), being a so-called pant product, or it may comprise fasteners, to fasten the front and back waist regions (or bands thereof).

For example, (re) fastenable diaper herein may have a front waist region (or band thereof) and a back waist region (or band thereof), whereby the front waist region (or band thereof) and back waist region (or band thereof) each have a first end portion and a second end portion and a middle portion located between the end portions, and whereby the end portions may include each a fastening system, to fasten the front waist band to the rear waist band or whereby the end portions may be connected to one another, and whereby the middle portion of the back waist band and/or the back region of the backsheet and/or the crotch region of the backsheet includes a landing member, wherein the landing member may include second engaging elements selected from loops, hooks, slots, slits, buttons, magnets. Examples include hooks, adhesive or cohesive second engaging elements. It may be that the engaging elements on the article, or diaper are provided with a means to ensure they are only engagable at certain moments, for example, they may be covered by a removable tab, which is removed when the engaging elements are to be engaged and may be re-closed when engagement is no longer needed, as described above.

Some diapers herein have one or more pairs of opposing leg cuffs and/or barrier cuffs, as known in the art, such cuffs comprising typically elastic material.

Methods:

The "WSP" standard methods referred to below are described in: "Standard Test Methods for the Nonwovens Industry", 2005 edition, jointly published by "Worldwide Strategic Partners" EDANA (European Disposables and Nonwovens Association, Avenue Eugene Plasky, 157, 1030 Brussels, Belgium, www.edana.org) and INDA (Association of the Nonwoven Fabrics Industry, 1100 Crescent Green, Suite 115, Cary, N.C. 27518, U.S.A., www.inda.org). This publication is available from EDANA or INDA.

The measurements should be carried out, unless otherwise stated, at an ambient temperature of 23±2° C. and a relative humidity of 50±10%. The water-absorbing material is thoroughly mixed through before measurement.

Centrifuge Retention Capacity (CRC)

Centrifuge Retention Capacity is determined by Standard Test WSP 241.2 "Fluid Retention capacity in Saline, after Centrifugation". In the following examples, however, the actual sample having the particle size distribution reported in the example was measured.

Absorbency Under Load (AUL)

Absorbency under Load is determined by Standard Test WSP 242.2 "Absorption under pressure, Gravimetric Determination". In the following examples, however, the actual sample having the particle size distribution reported in the example was measured.

Moisture Content

Water (or Moisture) Content is determined using Standard Test WSP 230.2 "Mass Loss upon Heating".

Fixed Height Absorption (FHA)

The FHA is a method to determine the ability of a swollen gel layer to transport fluid by wicking. It is executed and evaluated as described in WO 2009/016054 A2.

Saline Flow Conductivity

The method to determine the permeability of a swollen hydrogel layer is the "Saline Flow Conductivity" also known as "Gel Layer Permeability" is described in WO 2009/016054 A2.

16 h Extractables

The level of extractable constituents in the water-absorbing polymeric particles is determined by Standard Test WSP 270.2 "Extractables".

pH Value

The pH of the water-absorbing material is determined by Standard Test WSP 200.2 "pH of Polyacrylate (PA) Powders".

Free Swell Rate (FSR)

The method is described in WO 2009/016054 A2.

Particle Size Distribution (PSD)

The PSD is determined by Standard Test WSP 220.2 "Particle Size Distribution".

Flow Rate (FLR)

The Flow Rate is determined by Standard Test WSP 250.2 "Flow Rate, Gravimetric Determination".

Apparent Bulk Density (ABD)

The bulk density is determined by Standard Test WSP 260.2 "Density, Gravimetric Determination".

Cylinder Centrifuge Retention Capacity (CCRC)

The method is described in WO 2006/097389.

Core-Shell Absorbency Under Load (CS-AUL)

The method is described in WO 2006/097389.

Core-Shell Saline Flow Conductivity (CS-SFC)

The method is described in WO 2006/097389.

EXAMPLES

The examples designated as A are examples for the preparation of the base water-absorbing polymer.

The examples designated as B are preparation examples for the postcrosslinked water-absorbing polymer particles with a Centrifuge Retention Capacity (CRC) in the range from 26 to 30 g/g, an (AAP) of ≧21, a Fixed Height Absorption (FHA) of ≧21, a Saline Flow Conductivity (SFC) of ≧80, and an (FSR) of ≧0.10 according to the invention.

The examples designated with C describe the vacuum and optional plasma treatment.

Example A1

Preparation of Base Water-Absorbing Polymer

A Lödige VT 5R-MK plowshare kneader with 5 l capacity was charged with 206.5 g of deionized water, 271.6 g of acrylic acid, 2115.6 g of 37.3% by weight sodium acrylate solution (100 mol % neutralized) and also 1.288 g of a triply ethoxylated glycerol triacrylate crosslinker. This initial charge was inertized by bubbling nitrogen through it for 20 minutes. This was followed by the addition of dilute aqueous solutions of 0.618 g of sodium persulfate (dissolved in 13.9 g of water) and 0.013 g of ascorbic acid (dissolved in 10.46 g of water) to initiate the polymerization at about 20° C. After initiation, the temperature of the heating jacket was controlled to follow as close as possible (+/−0.5° C.) the reaction temperature inside the reactor. The crumbly gel ultimately obtained was then dried in a circulating air drying cabinet at 160° C. for about 3 hours.

The dried base polymer was ground and classified to 200-600 µm by sieving off over- and undersize particles.

The properties (averages) of the polymer were as follows:

Particle Size Distribution (Average):
<200 µm: 1.8% by weight
200-500 µm: 55.5% by weight
500-600 µm: 37.1% by weight
>600 µm: 5.5% by weight
CRC=35.6 g/g AUL 0.3 psi=17.9 g/g
16 h extractables=12.7% by weight
pH=5.9

Example B1

The base polymer being used here was prepared on the production scale in a batch kneader and corresponds to the base polymer according to example A1. It is characterized by the following data:
CRC=36 g/g
AUL 0.3 psi=16 g/g
PSD: >600 μm=6%
>500 μm=37%
>300 μm=44%
<300 μm=15%

In a pilot plant, this base polymer was sprayed with two surface postcrosslinking solutions and then heat-treated. The two solutions were sprayed on simultaneously in a Schuggi® Flexomix 100 D mixer with gravimetric dosage of the base polymer and continuous mass flow-controlled liquid dosage via two two-substance nozzles. The postcrosslinker solution I was sprayed on via a fine liquid nozzle (type J-2850-SS+gas nozzle J-73328-SS), which is arranged offset by 90° (based on the base polymer introduction site), while the postcrosslinker solution (or dispersion) II was sprayed on via a coarser liquid nozzle (type J-60100-SS+gas nozzle J-125328-SS), which is arranged offset by 270° (based on the base polymer introduction site). The nozzle types used are produced by Spraying Systems Deutschland GmbH. The spray gas used was nitrogen with a pressure of in each case 2 bar.

All quantitative data which follow are based on base polymer used. The postcrosslinker solution I comprised 0.83% by weight of water, 0.87% by weight of isopropanol, 0.05% by weight of 2-hydroxyethyloxazolidinone, 0.05% by weight of propanediol-1,3 and 0.008% by weight of Span 20 (sorbitan monolaurate). The postcrosslinker solution (or suspension) II comprised 0.3% by weight of water, 1.2% by weight of aluminum lactate solution 25% (Lohtragon® AL 250 from Dr. Paul Lohmann GmbH, Germany) and 0.3% by weight of tricalcium phosphate C53-80 (Chemische Fabrik Budenheim KG, Germany). The tricalcium phosphate was first dispersed in water and the aluminum lactate solution was dispersed with a high-speed stirrer (Turrax) and kept homogeneous by stirring in an appropriate reservoir vessel. The two postcrosslinker solutions were sprayed onto the base polymer, solution I at a rate of 1.446 kg/h, solution II at a rate of 1.44 kg/h, which corresponds to a loading of the base polymer of from 3.6 to 3.7% by weight based on the polymer. The moist polymer was transferred directly falling out of the Schuggi mixer into a NARA® NPD 1.6 W reaction drier. The base polymer throughput rate was approx. 80 kg/h and the product temperature of the steam-heated drier at the drier outlet was approx. 193° C. The setting of the drier with an inclination in the direction of the outlet of 3°, a weir height of approx. 64 mm, which corresponds to a fill level of approx. 95%, and a rotation speed of the shaft of approx. 14 rpm established a mean residence time of the product in the drier of approx. 35 minutes. Connected downstream of the drier was a cooler which cooled the product rapidly to approx. 50° C. Before being transferred to a transport container, the polymer was also passed through a screening machine equipped with two screening decks (150 μm/710 μm), and approx. 10% polymer (based on base polymer used) was removed predominantly as coarse material.

The resulting end product had the following properties (mean from 30 samples):
CRC=27.6 g/g
AUL 0.7 psi=24.5 g/g
SFC=129×10$^{-7}$ cm$^3$ sg$^{-1}$
FSR=0.2 g/g s
FHA=22 g/g
FLR=9.5 g/s
ABD=0.65 g/cm$^3$
PSD: >600 μm=1%
>500 μm=21%
>300 μm=46%
>150 μm=31%
<150 μm=1%

Example C1

Vacuum and Plasma Treatment

A sample of the product from example B1 described was plasma-treated in a "Pico LF-UHP D" laboratory plasma unit from Diener Electronic GmbH+Co. KG (TalstraBe 5, 72202 Nagold, Germany). To this end, at ambient temperature (23±2° C.), a 20 g sample was filled into a glass bottle which formed part of the equipment provided and was clamped unsealed in the plasma unit. The vacuum pump belonging to the plasma unit was switched on and run at maximum power. At a pressure of 0.6 mbar, air as the working gas with a gas flow of 400 ml/minute was switched on. Once the pressure had fluctuated and again reached a constant value (approx. 5 minutes), the plasma generator was switched on and run at 100% power. In the working state, the polymer-filled glass bottle is subject to a slow rotation which is predetermined by the unit and is not variable. Under these conditions, the sample was treated for 30 minutes, in the course of which the polymer was heated. Thereafter, the plasma generator was switched off and the sample was vented and the pressure was equalized to standard pressure with air. The following FHA and FSR values were determined before the plasma treatment of product B1 and after the vacuum and plasma treatment (product C1) using samples:

| Example | FHA [g/g] | FSR [g/g/s] |
| --- | --- | --- |
| B1 | 22.4 | 0.20 |
| C1 | 24.8 | 0.25 |

Example B2

Coating of Polymer as of Example A1

Preparation of the coating suspension (I) was as follows:
23.65 g of water,
6.00 g of tricalcium phosphate (C53-80 from Cfb BUDENHEIM, Germany),
12.55 g of isopropanol,
0.84 g of 1,3-propanediol,
0.85 g of N-(2-hydroxyethyl)-2-oxazolidinone,
0.036 g of sorbitan monolaurate (ALDRICH) and
1.14 g of a 10.5% by weight aqueous solution of polyvinylformamide/vinylamine (molar ratio 1:1) (Luredur® PR 8097 from BASF SE, Germany)

The components were charged in a beaker and homogenized for about one minute with an Ultraturrax (IKA Type TP18/10, Shaft: S25N-10G).

Preparation of the hydrophobic coating dispersion (II) was as follows:

3.16 g of a 38% by weight aqueous anionic, aliphatic polyurethane dispersion from BASF AG, Germany, based on polyetherols, pH ~8 (Astacin® Finish PUMN TF) and 6.97 g of water.

The components were charged in a beaker and stirred for few minutes with standard lab stirring equipment until a homogeneous dispersion was obtained.

A Lödige plowshare mixer of capacity 5 l was charged at room temperature with 1200 g of base polymer according to example A1. At a speed of 200 rpm 45.06 g of the coating suspension (I) and 10.13 g of the coating dispersion (II) were sprayed independently but in parallel onto the polymer particles within about 10 minutes, each via a 2-substance nozzle while using nitrogen of pressure 1 bar as atomizing gas and using a peristaltic pump for feeding the coating suspension.

Directly after coating was finished the coated polymer particles were transferred into a second, already preheated Lödige plowshare mixer of capacity 5 l (thermostat temperature 245° C.) and heated up to product temperature 190° C. for 35 minutes with nitrogen inertization. With increasing product temperature, coming closer to target temperature the thermostat set-temperature was reduced to 215° C. and kept unchanged until end of the run. To eliminate possible formation of agglomerates the surface crosslinked polymer particles were sieved on completion of heat treatment and before characterization over a 600 µm screen.

The coated material was subsequently tested for performance.

SFC: $207 \times 10^{-7}$ [cm$^3$ s/g]
AUL: 23.0 g/g
CRC: 28.2 g/g
FSR: 0.21 g/g/s
FHA: 17 g/g

Example C2

A sample of the product of example B2 described was treated with plasma entirely analogously to example C1. The following values were measured:

| Example | FHA [g/g] | FSR [g/g/s] |
|---|---|---|
| B2 | 17.0 | 0.20 |
| C2 | 24.6 | 0.21 |

Example B3

Coating of ASAP 510 Z (commercial product) with Astacin® PUMN TF:

The 150-500 µm fraction was sieved out of the commercially available product ASAP 510 Z (BASF SE) having the following properties and was then coated with Astacin PUMN TF according to the procedure below:

ASAP 510 Z (properties of the 150-500 µm fraction only):
CCRC=25.4 g/g
CS-AUL 0.7 psi=23.9 g/g
CS-SFC=$55 \times 10^{-7}$ [cm$^3$ s/g]

For the coating a Wurster laboratory coater from Waldner was used without using a Wurster tube. 2000 g per batch of super absorbent polymer ASAP 510 Z (commercially available product of BASF SE) of the particle distribution 150-500 µm were used. The Wurster apparatus was cone-shaped with a lower diameter at the bottom of 150 mm expanding to an upper diameter of 300 mm, the carrier gas was nitrogen having a temperature of 30° C., and the gas flow speed was 1.4 m/s at a pressure of 2 bar. The plate of the apparatus had drill holes of diameter 1.5 mm and an effective open cross-section for through-air-flow of 4.2%.

The coating agents (polymer dispersion: Polyurethane Astacin PUMN TF, BASF SE; deagglomeration agent: Silica sol LEVASIL® 50, H.C. Starck GmbH) have been atomized and spray-coated using a nitrogen-driven two-material nozzle from Schlick (Germany) operated in bottom spray mode, opening diameter 1.2 mm, the nitrogen temperature being 25° C. The coating agents have been sprayed each as a 20% by weight aqueous dispersion at a temperature of 23° C. First the aqueous polymer dispersion has been sprayed on, followed immediately thereafter by the aqueous dispersion of the deagglomeration aid.

Based on the weight of the absorbent polymer 2.0 wt. % (calculated as 100% solid) Astacin PUMN TF and 0.5 wt. % (calculated as 100% solid) Levasil® 50 have been used for coating. Spraying time has been 30 minutes for the polymer dispersion and 5 minutes for the deagglomeration aid.

The coated material was subsequently removed and has been transferred into a second laboratory fluidized bed dryer in which it has been held and heat treated at 168-170° C. (product temp.) for 40 minutes under nitrogen flow (gas inlet temp. about 30° C. higher than product temp.). Thereafter it was immediately poured onto a stainless steel tray and allowed to cool down to room temperature. Lumps have been removed from the coated material by coarse sieving over a 1000 µm screen and the coated material was subsequently tested for performance.

CS-SFC: $452 \times 10^{-7}$ [cm$^3$ s/g]
CS-AUL: 22.7 g/g
CCRC (1 g/4 hrs): 24.9 g/g
CCRC (1 g/30'): 23.3 g/g
FSR: 0.03 g/g/s
FHA: 3.8 g/g

Example C3

Vacuum and Plasma Treatment

A sample of the product from B3 described above was treated with plasma entirely analogously to example C1. The following values were determined for the starting substance B3 and the end product C3. Aging tests were carried out with the end product C3. A sample of the end product C3 was stored in each case at room temperature and at 60° C., and the FHA and FSR were each determined using a sample at intervals of three months.

| Example | FHA (g/g) | FSR (g/g/s) |
|---|---|---|
| before vacuum and plasma treatment (B3) | 3.8 | 0.03 |
| after vacuum and plasma treatment (C3) | 6.7 | 0.10 |
| after approx. 3 months of storage, sample stored at RT | 6.7 | 0.10 |
| after approx. 3 months of storage, sample stored at 60° C. | 6.1 | 0.10 |
| after approx. 6 months of storage, sample stored at RT | 6.1 | 0.10 |
| after approx. 6 months of storage, sample stored at 60° C. | 6.0 | 0.10 |

Preparation Examples B4-11

Entirely analogously to preparation example B3, the following polymer dispersions were sprayed onto ASAP 510 Z (150-500 nm) instead of the 2.0 wt.-% of Astacin PUMN TF:

| | |
|---|---|
| Example B4: | Blend of 2.0% by weight (calculated as solids content 100 based on SAP **) of Astacin ® PUMN TF + 1.0% by weight of Corial ® Binder IF *) (calculated as solids content 100 based on SAP) |
| Example B5: | Blend of 0.5% by weight (calculated as solids content 100 based on SAP) Astacin ® PUMN TF + 0.25% by weight of Corial ® Binder IF *) (calculated as solids content 100 based on SAP) |
| Example B6: | Blend of 0.25% by weight (calculated as solids content 100 based on SAP) Astacin ® PUMN TF + 0.125% by weight of Corial ® Binder IF *) (calculated as solids content 100 based on SAP) |
| Example B7: | Blend of 0.125% by weight (calculated as solids content 100 based on SAP) Astacin ® PUMN TF + 0.5% by weight of Corial ® Binder IF *) (calculated as solids content 100 based on SAP) |
| Example B8: | 0.5% by weight (calculated as solids content 100 based on SAP) of Corial ® Binder IF *) |
| Example B9: | 1.0% by weight (calculated as solids content 100 based on SAP) of Corial ® Binder IF *) |
| Example B10: | 2.0% by weight (calculated as solids content 100 based on SAP) of Corial ® Binder IF *) |
| Example B11: | 1.5% by weight of Astacin ® PUMN-TF (calculated as solids content 100 based on the particles of example A1) + 2.5% by weight of Polyethylenglycol 400 (based on the solid content of Astacin PUMN-TF) coated onto the particles of example A1, via the process set out under example B2. |

*): Corial ® Binder IF is an aqueous copolymer dispersion from BASF AG, Germany, based on acrylic ester, acrylonitrile, (meth)acrylamide and acrylic acid with a solids content of 40% by weight.
**): SAP stands for water absorbing polymeric particle

Examples C4-C10

Vacuum and Plasma Treatment

A sample of each of the end products from preparation examples B4—was treated with vacuum and plasma entirely analogously to example C1. The following values for the end products were measured:

| Example | FHA [g/g] | FSR [g/g] |
|---|---|---|
| B4 | 2.9 | 0.045 |
| C4 | 5.8 | 0.096 |
| B5 | 3.5 | 0.085 |
| C5 | 8.8 | 0.162 |
| B6 | 4.0 | 0.081 |
| C6 | 10.6 | 0.182 |
| B7 | 4.2 | 0.073 |
| C7 | 13.6 | 0.172 |
| B8 | 3.9 | 0.094 |
| C8 | 8.1 | 0.190 |
| B9 | 3.7 | 0.101 |
| C9 | 5.6 | 0.189 |
| B10 | 3.6 | 0.073 |
| C10 | 5.9 | 0.145 |
| B11 | 21.2 | |
| C11 | 23.9 | |
| B12 | 4.8 | |
| C12 | 9.9 | |

Example C 11

Vacuum and Plasma Treatment

A sample of the end product from preparation examples B 11 was treated with vacuum and plasma entirely analogously to example C1. The following values for the end products were measured:

| Example | FHA [g/g] |
|---|---|
| B11 | 4.8 |
| B10 | 9.9 |

Preparation Example B12

The base polymer being used here was prepared on the production scale in a batch kneader and corresponds to the base polymer according to example A1, except that the monomer concentration for the polymerization was 35.5 wt.-%, Sodium Persulfate amount was 0.122 wt.-% based on total Acrylic Acid, crosslinker amount was 0.375 wt.-% based on total Acrylic Acid and that instead of Ascorbic Acid it was used 0.04 wt.-% (based on total Acrylic Acid) of a reducing agent, which is a blend of 2-Hydroxy-2-sulfinatoaceticacid-Di-Na, 2-Hydroxy-2-sulfonatoaceticacid-Di-Na and Na-bisulfit and which is sold by the company BrüggemannChemical, L. Brüggemann KG, Germany under the trade name Bruggolite® FF7.

The dried base polymer was ground and classified to 150-710 μm by sieving off over- and undersize particles. It is characterized by the following data (averages):
CRC=36 g/g
AUL 0.3 psi=15 g/g
Extractables, 16 hrs=12%
PSD: >710 μm=≦1%
>600 μm=19%
>300 μm=65%
>200 μm=10%
>150 μm=4%
<150 μm=≦1%

In a pilot plant, this base polymer was at first sprayed with two surface post-crosslinking solutions and was then heat-treated. The two solutions were sprayed on simultaneously in a Schuggi® Flexomix 100 D mixer with gravimetric dosage of the base polymer and continuous mass flow-controlled liquid dosage via two two-substance nozzles. The post-crosslinker solution I was sprayed on via a fine liquid nozzle (type J-2850-SS+gas nozzle J-73328-SS), which is arranged offset by 90° (based on the base polymer introduction site), while the post-crosslinker solution (or dispersion) II was sprayed on via same liquid nozzle (type J-2850-SS+gas nozzle J-73328-SS), which is arranged offset by 270° (based on the base polymer introduction site). The nozzle types used are produced by Spraying Systems Deutschland GmbH. The spray gas used was nitrogen with a pressure of in each case 2 bar.

All quantitative data which follow are based on base polymer used. The post-crosslinker solution I comprised 0.97% by weight of isopropanol, 0.05% by weight of 2-hydroxy-ethyloxazolidinone, 0.05% by weight of propanediol-1,3, 0.008% by weight of Span 20 (sorbitan monolaurate) and 2.4% by weight of aluminum lactate solution 25% (Lohtragon® AL 250 from Dr. Paul Lohmann GmbH, Germany). The post-crosslinker solution (or dispersion) II comprised 0.23% by weight of water and 0.39% by weight of Astacin PUMN TF (BASF SE, Germany). The two post-crosslinker solutions were sprayed onto the base polymer, solution I at a rate of 2,782 kg/h, solution II at a rate of 0,496 kg/h, both at a base polymer throughput of 80 kg/h. The moist polymer was transferred directly falling out of the Schuggi mixer into a NARA® NPD 1.6 W reaction drier. The base polymer throughput rate was approx. 80 kg/h and the product temperature of the steam-heated drier at the drier outlet was approx. 196° C. The setting of the drier with an inclination in the direction of the outlet of 3°, a weir height of approx. 64 mm, which corresponds to a fill level of approx. 95%, and a rotation speed of the shaft of approx. 14 rpm established a mean residence time of the product in the drier of approx. 35 minutes. Connected downstream of the drier was a cooler which cooled the product rapidly to approx. 50° C. Before being transferred to a transport container, the polymer was also passed through a screening machine equipped with two screening decks (150 nm/710 nm), and approx. 19% polymer (based on base polymer used) was removed predominantly as coarse material.

The resulting end product had the following properties (mean from 30 samples):
CRC=27.0 g/g
AUL 0.7 psi=23.8 g/g
SFC=185×10-7 cm$^3$ sg-1
FSR=0.2 g/g s
FHA=21 g/g
FLR=10.2 g/s
ABD=0.68 g/cm$^3$
PSD: >710 μm=≦1%
   >600 μm=14%
   >300 μm=54%
   >150 μm=31%
   <150 μm=<1%

Example C12

A sample of the end product from preparation examples B 12 was treated with vacuum and plasma entirely analogously to example C1. The following values for the end products were measured:

| Example | FHA [g/g] |
|---------|-----------|
| B12     | 21.2      |
| C12     | 23.9      |

Examples C13-C15

For plasma treatment, the 300-600 μm particle fraction of a development product which had been prepared analogously to example B1, except without tricalcium phosphate, but had been coated with 0.6% by weight (based on water absorbing particles) of aluminum lactate, was used. The plasma treatment was effected as described in plasma example 1, except that the use amount of the product B1 and/or the plasma treatment time were varied, which can be discerned from the following table.

The following values were measured:

| Example | Amount of SAP | Plasma treatment time | FHA (g/g) | FSR (g/g/s) |
|---------|---------------|----------------------|-----------|-------------|
| Before plasma treatment Product B1 | — | — | 19.4 | 0.153 |
| C13 | 20 g | 30 minutes | 24.4 | 0.167 |
| C14 | 20 g | 1 minute | 23.7 | 0.161 |
| C15 | 100 g | 1 minute | 21.6 | 0.145 |

SAP: water absorbing particles

Examples C16-18

Only Vacuum Treatment

For plasma treatment, the 300-600 μm particle fraction of a development product which had been prepared analogously to example B1, except without tricalcium phosphate, but had been coated with 0.6% by weight (based on water absorbing particles) of aluminum lactate, was used. The treatment was effected as described in plasma example C1, except that the plasma generator was not switched on. The used amount of the product B1 and the vacuum treatment time are listed in the following table.

The following values were measured:

| Example | Amount of SAP | Vacuum treatment time | FHA (g/g) | FSR (g/g/s) |
|---------|---------------|----------------------|-----------|-------------|
| Before vacuum treatment | — | — | 19.4 | 0.153 |
| C16 | 100 g | 5 minutes | 17.8 | 0.155 |
| C17 | 100 g | 30 minutes | 18.8 | 0.165 |
| C18 | 20 g | 30 minutes | 16.8 | 0.167 |

SAP: water absorbing particles

Examples C19-23

Only Vacuum Treatment

For the vacuum treatment the same development product was been used as described in examples C13-18, but it was chosen now the particle size distribution cut 150-710 μm. Prior to the vacuum treatment water and/or a water miscible organic solvent was added to the water absorbing polymer in an amount given in the following table by weight of the water-absorbing particles. The vacuum treatment was effected as described in example plasma C1, except that the plasma generator was not switched on. The used amount of the product B1 and the vacuum treatment time are listed in the following table.

The following values were measured

| | Treatment prior to vacuum | Amount of SAP | Vacuum treatment time | FSR (g/g/s) |
|---|---|---|---|---|
| Before vacuum treatment | — | — | — | 0.152 |
| C19 | — | 20 g | 30 minutes | 0.163 |
| Before vacuum treatment | +2% water | — | — | 0.158 |

-continued

| | Treatment prior to vacuum | Amount of SAP | Vacuum treatment time | FSR (g/g/s) |
|---|---|---|---|---|
| C20 | +2% water | 20 g | 30 minutes | 0.161 |
| Before vacuum treatment | +2% Isopropanol | — | — | 0.153 |
| C21 | +2% Isopropanol | 20 g | 30 minutes | 0.162 |
| Before vacuum treatment | +1.4% water + 0.6% Isopropanol | — | — | 0.156 |
| C22 | +1.4% water + 0.6% Isopropanol | 20 g | 30 minutes | 0.166 |
| Before vacuum treatment | +0.6% water + 1.4% Isopropanol | — | — | 0.174 |
| C23 | | 20 g | 30 minutes | 0.187 |

SAP: water absorbing particles

Examples C24-32

Only Vacuum Treatment

For the vacuum treatment with reduced vacuum the same development product might be used as described in examples C17-21 in the same PSD-cut 150-710 µm. The vacuum treatment should be effected as described in example plasma C1, except that different vacuum levels should be hold and that the plasma generator should not be switched on.

The following amounts, vacuum levels and time should be chosen:

| | Amount of SAP | Vacuum level | Vacuum treatment time |
|---|---|---|---|
| Before vacuum treatment | — | — | — |
| C24 | 20 g | 1 mbar | 30 minutes |
| C25 | 20 g | 1 mbar | 1 minute |
| C26 | 20 g | 100 mbar | 30 minutes |
| C27 | 20 g | 250 mbar | 30 minutes |
| C28 | 20 g | 250 mbar | 10 minutes |
| C29 | 20 g | 250 mbar | 1 minute |
| C30 | 20 g | 500 mbar | 30 minutes |
| C31 | 20 g | 700 mbar | 30 minutes |

SAP: water absorbing particles

Comparative Example B13 with Aerosil 200

The sample B12 as described above was treated with Aerosil 200 (as available from for example BASF, Germany), a hydrophilic silica-based coating agent, by applying this as an aqueous spray-on dispersion, to obtain a 1% by weight of the A1 particles of Aerosil 200 coating. Sample B13 with this Aerosil 200 coating showed a FHA value of 17.4 g/g, which was significantly less than the FHA of the coated example C12 (23.9 g/g).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent structure comprising vacuum-treated, post-crosslinked water-absorbing polymeric particles, obtainable by a process comprising the steps of:
   a) obtaining post-crosslinked water-absorbing polymeric particles; and
   b) exposing the particles of step a) to a vacuum-treatment, at a pressure from about 0.0001 mbar to about 700 mbar;
   wherein prior to, simultaneously with, or subsequently to step b), the post-crosslinked water-absorbing polymeric particles are treated by exposing the particles to a plasma-treatment.

2. An absorbent structure according to claim 1, wherein the post-crosslinked water-absorbing polymeric particles are coated with a coating agent prior to, simultaneously with, or subsequently to cross-linking.

3. An absorbent structure according to claim 1, wherein the post-crosslinked water-absorbing polymeric particles of step a) are obtained by:
   a) polymerization of a monomer solution comprising at least one of the following:
      i) an ethylenically unsaturated acid functional monomer,
      ii) an ethylenically unsaturated crosslinker,
      iii) one or more ethylenically and/or allylically unsaturated monomers copolymerizable with i), and
      iv) one or more water-soluble polymers grafted wholly or partly with the monomers of i), ii) and/or iii),
      to obtain base water-absorbing polymers;
   b) post-crosslinking the base water-absorbing polymers with a post-crosslinking agent; and
   c) forming particles of the polymers of step a) or b) above.

4. An absorbent structure according to claim 3, wherein step a) of claim 3 is conducted in the presence of a non radical crosslinking agent, having in its single molecule two or more functional groups, each of which allows formation of an ester or an amide bond by reaction with carboxyl groups.

5. An absorbent structure according to claim 2, wherein the post-crosslinked water-absorbing polymeric particles are coated with a water soluble polyvalent metal salt, to obtain coated post-crosslinked water-absorbing polymeric particles.

6. An absorbent structure according to claim 2, wherein the post-crosslinked water-absorbing polymeric particles are coated with a water-insoluble metal phosphate, to obtain coated post-crosslinked water-absorbing polymeric particles.

7. An absorbent structure according to claim 2, wherein the post-crosslinked water-absorbing polymeric particles are coated with a film forming polymer, to obtain coated post-crosslinked water-absorbing polymeric particles.

8. An absorbent structure according to claim 7, wherein the film forming polymer has a minimum film forming temperature above about −10° C.

9. An absorbent structure according to claim 7, wherein the film forming polymer comprises, or is, polyurethane polymer.

10. An absorbent structure according to claim 7, wherein the film forming polymer is applied by a step including an annealing heat treatment step.

11. An absorbent structure according to claim 1, wherein the post-crosslinked water-absorbing polymeric particles of step a) are treated with about 0.1 to about 5 weight-% water and/or water miscible organic solvents prior to step b).

12. An absorbent structure according to claim 1, wherein the vacuum-treatment step b) is performed at a pressure from about 0.0001 mbar to about 20 mbar, and over a period of about 0.1 seconds to about 30 minutes.

13. An absorbent structure according to claim 1, wherein the plasma-treatment step is performed prior to or subsequently to step b) and under ambient atmospheric pressure.

14. An absorbent structure according to claim 1, wherein the plasma is an air-plasma.

15. An absorbent structure according to claim 1, being an absorbent core of an absorbent article, comprising: a) at least about 50% (by weight of the absorbent structure) of the vacuum-treated, post-crosslinked water-absorbent polymeric particles; and b) a non-absorbent fibrous material and/or an adhesive material.

16. An absorbent structure according to claim 15, wherein component b) comprises a non-absorbent fibrous thermoplastic adhesive material, and it is present in an amount such that the weight ratio of a) to b) is from about 40:1 to about 3:1.

17. An absorbent article selected from adult incontinence garments, infant diapers, feminine hygiene articles, comprising an absorbent structure according to claim 1.

18. An absorbent article according to claim 17, wherein the article is an infant diaper.

19. An absorbent structure according to claim 1, wherein the pressure is from about 0.0001 mbar to about 400 mbar.

20. An absorbent structure according to claim 19, wherein the pressure is from about 0.0001 mbar to about 1 mbar.

21. An absorbent structure according to claim 1, wherein the vacuum-treated post-crosslinked water-absorbing polymeric particles have a Centrifuge Retention Capacity of at least about 25 g/g.

22. An absorbent structure according to claim 1, wherein the vacuum-treated post-crosslinked water-absorbing polymeric particles have an Absorbency Under Load of at least about 19 g/g.

23. An absorbent structure according to claim 1, wherein the vacuum-treated post-crosslinked water-absorbing polymeric particles have a Saline Flow Conductivity of at least about $150 \times 10^{-7} cm^3 s/g$.

24. An absorbent structure according to claim 1, wherein the vacuum-treated post-crosslinked water-absorbing polymeric particles have a Fixed Height Absorption of at least about 12 g/g.

25. An absorbent structure according to claim 2, wherein the coated post-crosslinked water-absorbing polymeric particles of step a) are treated with about 0.1 to about 5 weight-% water and/or water miscible organic solvents prior to step b).

* * * * *